(12) United States Patent
Shirouzu et al.

(10) Patent No.: US 7,253,144 B2
(45) Date of Patent: Aug. 7, 2007

(54) METHOD FOR PRODUCING BY CELL-FREE PROTEIN SYNTHESIS SYSTEM USING THIOREDOXIN-FUSED PROTEIN EXPRESSION VECTOR

(75) Inventors: Mikako Shirouzu, Yokohama (JP); Goushi Ishihara, Yokohama (JP); Mihoro Saeki, Yokohama (JP); Mie Goto, Yokohama (JP); Kaori Tajima, Yokohama (JP); Takanori Kigawa, Yokohama (JP); Shigeyuki Yokoyama, Yokohama (JP)

(73) Assignee: Riken, Wako-Shi, Saitama (JP)

( * ) Notice: Subject to any disclaimer, the term of this patent is extended or adjusted under 35 U.S.C. 154(b) by 0 days.

(21) Appl. No.: 10/992,360

(22) Filed: Nov. 19, 2004

(65) Prior Publication Data

US 2005/0255542 A1 Nov. 17, 2005

Related U.S. Application Data

(63) Continuation of application No. PCT/JP03/06314, filed on May 21, 2003.

(30) Foreign Application Priority Data

May 22, 2002 (JP) ............................. 2002-148135

(51) Int. Cl.
| | | |
|---|---|---|
| C12N 15/70 | (2006.01) | |
| C12N 15/63 | (2006.01) | |
| C07K 14/705 | (2006.01) | |
| C07K 21/04 | (2006.01) | |
| A61K 38/00 | (2006.01) | |

(52) U.S. Cl. .................. 514/2; 536/23.1; 530/412; 530/350; 435/69.1; 435/7.2; 435/69.7

(58) Field of Classification Search ............... 536/23.1; 530/412, 350; 435/69.1, 440, 69.7, 195, 435/68.1, 7.2; 514/2; 424/192.1
See application file for complete search history.

(56) References Cited

U.S. PATENT DOCUMENTS

| 5,270,181 | A | | 12/1993 | McCoy et al. | |
|---|---|---|---|---|---|
| 5,532,151 | A | * | 7/1996 | Chantry et al. | ............. 435/194 |
| 2002/0142387 | A1 | | 10/2002 | Seki et al. | |

FOREIGN PATENT DOCUMENTS

| EP | 1 143 009 A1 | | 10/2001 |
|---|---|---|---|
| EP | 1 176 210 A1 | | 1/2002 |
| EP | 1 354 959 A1 | | 10/2003 |
| JP | 9-107954 A | | 4/1997 |
| WO | WO 9213955 | * | 8/1992 |
| WO | WO 99/02671 A1 | | 1/1999 |
| WO | WO 02/090537 A1 | | 11/2002 |

OTHER PUBLICATIONS

Liu et al. (Feb. 2001) Functional characterization of novel human ARFGAP3. FEBS Lett. vol. 490, Nos. 1-2, pp. 79-83.*
Laage et al. (2001) Strategies for prokaryotic expression of eukaryotic membrane proteins. Traffic, vol. 2, No. 2, pp. 99-104.*
Yoshida et al. (2000) In vitro synthesis of hyaluronan by a single protein derived from mouse HAS1 gene and characterization of amino acid residues essential for the activity. J. Biol. Chem. vol. 275, No. 1, pp. 497-506.*
Lehto et al. (1998) Release of the glycosylphosphatidylinositol-anchored enzyme ecto-5'-nucleotidase by phospholipase C: catalytic activation and modulation by the lipid bilayer. Biochem. J. vol. 332 (Pt 1), pp. 101-109.*
The pET Expression system (2003) The pET Expression system, http://www.bio.davidson.edu/Course/Molbio?nolStudents/spring2003/Causey/pET.html, pp. 1-4.*
Tucker et al. (1996) Purification of a rat neurotensin receptor expressed in *Escherichia coli*. Biochem. J. vol. 317 (Pt 3), pp. 891-899.*
Grisshammer et al. (1993) Expression of a rat neurotensin receptor in *Escherichia coli*. Biochem. J. vol. 295 (Pt 2), pp. 571-576.*
Abdulaev et al. Functionally discrete mimics of light-activated rhodopsin identified through expression of soluble cytoplasmic domains. J. Biol. Chem. vol. 275, pp. 39354-39363.*
Sachev et al. (1998) Solubility of proteins isolated from inclusion bodies is enhanced by fusion to maltose-binding protein or thioredoxin. Protein Expr. Purif. vol. 12, No. 1, pp. 122-132.*
McIntyre et al. (1991) Procapthesins L and D are membrane-bound in acidic microsomal vesicles. J. Biol. Chem. vol. 266, No. 23, pp. 15438-15445.*
Invitrogen (2002) Flexible in vitro expression with high-yield results, Expressions, vol. 9 issue 2, p. 7.*
Novagen (1998) pET-23a-b(+)vectors, p. 1.*
Falk et al. (1997) Cell-free synthesis and assembly of connexins into functional gap junction membrane channels.☐☐EMBO J. vol. 16, No. 10, pp. 2703-2716.*
Rhee et al. (1996) Channel-forming activity of immunoaffinity-purified connexin32 in single phospholipid membranes. Biochemistry. vol. 35, No. 28, pp. 9212-9223.*

(Continued)

*Primary Examiner*—Karen Cochrane Carlson
*Assistant Examiner*—Samuel W. Liu
(74) *Attorney, Agent, or Firm*—Birch, Stewart, Kolasch & Birch, LLP

(57) ABSTRACT

We claim a method of expression a thioredoxin-fused membrane protein comprising expressing said thioredoxin-fused membrane protein in a cell-free protein synthesis system in the presence of a non-ionic detergent. It is preferable that the fused membrane protein which is a highly hydrophobic protein, e.g., a G protein-coupled receptor, can be produced in a state being highly soluble and capable of forming a biologically active three-dimensional structure. Also, this invention provides a recombinant polynucleotide encoding said thioredoxin-fused membrane protein which is expressed in the cell-free protein synthesis system.

16 Claims, 11 Drawing Sheets

OTHER PUBLICATIONS

Ohtaki et al. (1998) Expression, purification, and reconstitution of receptor for pituitary adenylate cyclase-activating polypeptide. large-scale purification of a functionally active G protein-coupled receptor produced in Sf9 insect cells. J. Biol. Chem. vol. 273, No. 25, pp. 15464-15473.*

Mambetisaeva et al. (1997) Expression of three functional domains of connexin 32 as thioredoxin fusion proteins in *Escherichia coli* and generation of antibodies. Protein Expr. Purif. vol. 11, No. 1, pp. 26-34.*

Peng et al. (1998) Cystic fibrosis transmembrane conductance regulator: expression and helicity of a double membrane-spanning segment. FEBS Lett. vol. 431, No. 1, pp.29-33.*

Sigma-Aldrich product catalog page for Polyoxyethlene 23 lauryl ether (Brij 35).

E. Bochkareva et al., The Journal of Biological Chemistry, vol. 271, No. 36, Sep. 1996, pp. 22256-22261.

N. Nishimura et al., Journal of Fermenation and Bioengineering, vol. 80, No. 4, 1995, pp. 403-405.

T. Kigawa et al., FEBS Letters, vol. 442, 1999, pp. 15-19.

P.J. Booth et al., Biochemical Society Transactions, vol. 28, Part 3, 2000, p. A50.

Shuyun Peng et al., FEBS Letters, vol. 431, No. 1, pp. 29-33 (1998).

* cited by examiner

METHOD FOR PRODUCING BY CELL-FREE PROTEIN SYNTHESIS SYSTEM USING THIOREDOXIN-FUSED PROTEIN EXPRESSION VECTOR

This application is a Continuation of co-pending PCT International Application No. PCT/JP03/06314 filed on May 21, 2003, which designated the United States, and on which priority is claimed under 35 U.S.C. § 120, which claims priority under 35 U.S.C. § 119(a) on Patent Application No(s). 2003-148135 filed in Japan on May 22, 2002, the entire contents of which are hereby incorporated by reference.

TECHNICAL FIELD

The present invention relates to a method for producing a protein by cell-free protein synthesis system, and more particularly to a method for producing a highly hydrophobic protein such as a membrane protein as a soluble protein by cell-free protein synthesis system.

BACKGROUND ART

Recently, DNA sequences of various organisms including human have been analyzed increasingly and rapidly, and with regard to a large number of genes extracted from this enormous genome sequence information, a research called "Structural genomics" became an important field, which is a systematic and comprehensive analysis of the relationship between structure and function of proteins by determining three dimensional structure of proteins encoded by individual genes. In addition, a high-throughput analytical means applicable to a large scale analysis for promoting such a research is desired.

In this "Structural genomics", a most important target as a pharmaceutical development among the proteins for their structural analysis may for example be a membrane protein. While a membrane protein is responsible for important cellular functions such as a response to a stimulation, cellular skeleton and adhesion, material transportation and electron transport, it is difficult to be analyzed biochemically because of an extreme difficulty in its isolation and purification.

When a membrane protein is expressed in a cultured cell, it is accumulated in the cell membrane as a result of a localization function of the host cell. Thus, in a purification step of the resultant protein, it is necessary to extract the membrane protein from the cell membrane using various solubilizing agents, which is time-consuming and laborious and also involves a problem with regard to the extraction efficiency. Moreover, some types of the solubilizing agents may deteriorate the structure or function associated naturally with the protein.

On the other hand, a membrane protein, when expressed in E. coli, frequently precipitates as insolubles, which leads to a purification requiring a precipitation solubilizing step employing a potent denaturating agent such as guanidine or urea and a step for recovering the native structure (folding) of the protein which has once been denatured in the preceding solubilization step. These steps are problematic not only in view of the time and the labor but also in view of re-insolubilization occurring during the above-mentioned folding step.

In order to avoid these problems, a prior art employed a method for co-expressing an E. coli heat shock chaperone or foldase with a heterologous gene. For example, JP-A-9-107954 discloses, as this heat shock chaperone, heat shock proteins such as E. coli GroES and GroEL, which serves to catalyze a correct folding of a polypeptide which has been newly synthesized in E. coli. On the other hand, a foldase such as a protein disulfide isomerase or peptidylproryl cis-trans isomerase is disclosed, and an over-co-expression of these chaperone and foldases, especially an E. coli thioredoxin, allows a mouse c-Myb or human transcription factor cAMP-responding element-binding protein or p53 anticancer gene product to be expressed as a soluble protein at a level of several ten mg to 100 mg per 1 liter of an E. coli culture.

Still another method is a method for allowing an intended heterologous gene to be expressed as a fusion protein with another protein. This another protein may for example be glutathione S-transferase (GST), maltose binding protein (MBP), protein A or protein G, and a target protein is expressed usually as a protein fused with the C terminal any of these proteins (see JP-A-9-107954, supra).

However, any of these methods is still problematic because it allows a highly hydrophobic protein such as a membrane protein to be aggregated readily in E. coli cells upon expression and also because it enables the expression only at an extremely low level.

Under the circumstance discussed above, an objective of the invention is to provide a method for producing a highly hydrophobic protein such as a membrane protein in a state allowing the solubilization to be accomplished very easily and also in a state allowing a biologically active three dimensional structure to be formed.

DISCLOSURE OF THE INVENTION

In order to solve the problems mentioned above, the present inventors have made an effort and finally discovered that by expressing a fusion protein of a thioredoxin with a target protein in a cell-free protein synthesis system, a large amount of the protein can be expressed at an extremely high efficiency, and that at least a part of the fusion protein can be obtained as a soluble protein without aggregation even when the target protein is a highly hydrophobic protein such as a membrane protein. The inventors also discovered that the fusion protein thus obtained or the target protein isolated by a limited digestion of the fusion protein has at least a part of the biological activity associated naturally therewith and can form a correct three dimensional structure. These findings have led to the completion of the present invention.

Thus, in one aspect, the present invention is characterized by expressing a fusion protein of a thioredoxin with a membrane protein in a cell-free protein synthesis system. In a preferred embodiment of the present invention, the cell-free protein synthesis system comprises a detergent, whereby further increasing the solubilization rate of the fusion protein. Accordingly, it is highly possible that a thioredoxin-fused membrane protein synthesized by an inventive method forms a correct three dimensional structure, which stabilizes the structure of the protein and also allows the expression level to be increased while improving the solubility.

In one embodiment of the present invention, the membrane protein includes a receptor protein, channel protein and transporter protein, and similarly to these proteins, a transcription factor, signal transducing protein, drug metabolism enzyme and lipid metabolism enzyme may also be applicable to the invention.

In another embodiment of the present invention, the thioredoxin is an E. coli thioredoxin, mammalian thioredoxin or yeast thioredoxin, including a polypeptide derived from the polypeptide by deletion, addition or substitution of one or several amino acids in the amino acid sequence thereof, which is capable of solubilizing at least a part of the fusion protein described above.

Also in a preferred embodiment of the present invention, the thioredoxin-fused membrane protein is a fusion protein which can be synthesized at a synthetic yield of at least 100 µg/ml within a reaction period of 8 hours in a cell-free protein synthesis system. While such a cell-free protein synthesis system may be any of various methods such as a batch method or dialysis method, usually the dialysis method exhibits a higher synthetic yield of the protein. In this embodiment, it is sufficient to obtain an expression level of at least 100 µg/ml in any of these various synthesis methods, and a protein synthesis yield can be checked by an appropriate sampling at any time point within 6 to 8 hours after initiation of the synthesis reaction. Also by selecting a preferable system, the thioredoxin-fused membrane protein described above can be synthesized at a synthetic yield of at least 500 µg/ml, preferably about 1 mg/ml or more within a reaction period of 6 to 8 hours in the cell-free protein synthesis system.

A method for producing a membrane protein is also provided in which a thioredoxin-fused membrane protein synthesized by any method described above is further digested limitedly to isolate the membrane protein.

In another aspect of the present invention, there is provided a polynucleotide for expressing a fusion protein gene in a cell-free protein synthesis system, said polynucleotide comprising a thioredoxin gene linked via a ribosome binding site downstream of a T7 promoter sequence and a membrane protein gene linked with the thioredoxin gene to be expressed as a fusion protein, wherein no operator sequence is contained near the promoter sequence.

In still another aspect of the present invention, there is provided a plasmid vector comprising, in a 5' to 3' direction, a T7 promoter sequence, a ribosome binding site, multiple cloning sites and a transcription termination sequence, wherein a thioredoxin gene is contained adjacently to the upstream or downstream of the multiple cloning site and no operator sequence is contained near the promoter sequence.

In another embodiment of the present invention, a method for producing a fusion protein comprising expressing a fusion protein of a thioredoxin with a target protein in a cell-free protein synthesis system, wherein at least a part of the fusion protein is synthesized as a soluble protein is also provided.

In still another aspect, there is provided a method for producing a complex of a thioredoxin-fused membrane protein and a liposome comprising the steps of: ligating a thioredoxin gene to a membrane protein gene, expressing the ligated gene in a cell-free protein synthesis system, mixing a protein expressed in the cell-free protein synthesis system with a detergent and a liposome whose particle size is uniform, and reducing the concentration of the detergent in the mixture. The particle size of the liposome is preferably within the range of 50 to 200 nm, more preferably 80 to 150 nm, most preferably about 100 nm.

BRIEF DESCRIPTION OF THE DRAWINGS

FIG. 9 A-B shows the expression levels of various thioredoxin-fused or non-fused β2AR proteins synthesized in a cell-free protein synthesis system by a batch method.

FIG. 11 B shows the results of the optimization of the levels of digitonin and Brij 35 to be added, with a solid bar representing a total synthesized protein level and an open bar representing a supematant protein level.

FIG. 13 A-B shows the change in the synthesis level of β2AR in a cell-free protein synthesis system by a dialysis method.

FIG. 14 A-B shows the ligand binding activity of reconstituted β2AR-Gs.

Figure 1:
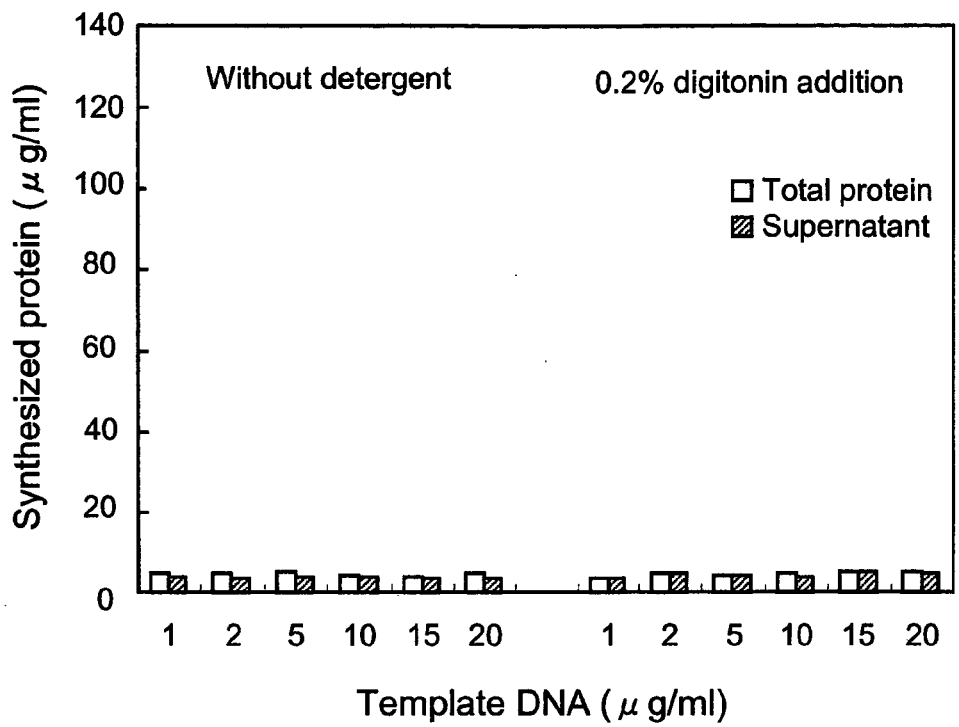
FIG. 1 shows the results of the expression of MT43-NTR in a cell-free protein synthesis system by a batch method.

BEST MODE FOR CARRYING OUT THE INVENTION (Target Protein)

While a target protein in an inventive method includes but not limited to an *E. coli* protein, yeast protein or mammalian protein, an insoluble protein containing a highly hydrophobic moiety locally in its molecule may for example be capable of exhibiting a satisfactory result. As used herein, a "protein" means a polypeptide comprising two or more amino acids linked via a peptide bond to each other, and is generally one having several tens or more of constituted amino acids. A "protein" or "polypeptide" includes an amino acid sequence modified by natural process such as a post translational processing after translation or a chemical modification known in the art. The modification may occur at any position in a protein including a peptide backbone, amino acid side chain or amino terminal or carboxyl terminal.

In a preferred embodiment of the invention, a target protein may be a membrane protein such as a receptor protein, channel protein and transporter protein as well as a transcription factor, antibody, signal transducing protein and the like, any of which is an important protein as a pharmaceutical development. As used herein, a "membrane protein" is an intrinsic membrane protein as well as those which are palmitoylated, geranylated or myristoylated and whose modified moiety is embedded in a membrane lipid, or those which are undergoing an interaction with the membrane lipid or membrane protein. An extremely water insoluble property is exhibited especially by an intrinsic membrane protein having a transmembrane site because of the presence of a hydrophobic amino acid sequence aligned so that integration into the membrane lipid can readily be achieved. Since these membrane proteins are readily aggregated and form insoluble precipitations when they are expressed in heterologous hosts using a recombinant DNA technology, it is difficult to prepare a protein which is biologically active and has a correct three dimensional structure. Nevertheless, many of these membrane proteins play important roles such as intracellular signal transduction and growth regulation, and thus are very important targets in the pharmaceutical field.

A signal transduction pathway is a medically important biological pathway which is regulated by a second messenger such as a G protein and cAMP. As used herein. "G protein" refers to a trimeric guanine nucleotide binding protein consisting of α, β and γ subunits. A protein involved in this signal transduction pathway may for example be a G protein-coupled receptor (GPCR) which binds to a ligand such as a peptide hormone and a neurotransmitter, a G protein itself, an effecter protein such as phospholipase C, adenylate cyclase, phosphodiesterase and the like, as well as protein kinase A and protein kinase C.

A GPCR super family as membrane proteins is called also as a seven membrane-spanning receptor since it has seven α-helix transmembrane moieties. A G protein to be coupled is usually a trimer, consisting of α, β and γ subunits. An extremely large number of ligands are known to bind with the GPCR, including dopamine, adrenaline, endothelin, adenosine, muscarine, acetylcholine, serotonin, histamine, thrombin, kinin, gustatory component and olfactory component. To control the activity of such a receptor is effective in treating a disease relating to nerve, immune, blood pressure and metabolism. While genome analysis of eukaryotic organisms identified a large number of receptors and a comprehensive research tool is desired, the GPCR problematically tends to be aggregated easily when expressed in a large amount by a prior art since it is extremely hydrophobic due to its structure having seven membrane-spanning regions.

Accordingly, in one embodiment of the invention, a method for producing a thioredoxin-fused GPCR comprising expressing a fusion protein of a thioredoxin with a GPCR which is a target protein in a cell-free protein synthesis system is provided. A thioredoxin-fused GPCR produced by this method can readily be solubilized using a detergent without aggregation and/or can be re-constituted into a receptor protein having a signal transducing function by mixing with a lipid component. The GPCR can be examined for its signal transducing function using various method, for example by measuring its ligand binding activity or its G protein activity. As used herein, the GPCR includes those formed as a result of deletion, addition or substitution of one or more (several) amino acids in a naturally occurring GPCR but still having the signal transducing function possessed by the relevant GPCR. Those also included are other peptide sequence such as fused proteins with G protein. A GPCR according to the invention may be a protein derived from cells (for example, hepatocyte, splenic cell, neurocyte, gliacyte, pancreatic beta cell, myelocyte, mesangial cell, Langerhans' cell, epidermic cell, epithelial cell, endothelial cell, fibroblast, myocyte, adipocyte, immunocyte, or their precursor cells, stem cells or carcinomatous cells and the like) of a human or warm-blooded animal (for example, guinea pig, rat, mouse, chicken, rabbit, pig, sheep, cattle, monkey and the like) or from various tissues in which these cells exist (for example, brain, spinal cord, pituitary gland, stomach, pancreas, kidney, liver, gonad, thyroid gland, gallbladder, bone marrow, adrenal gland, skin, muscle, lung, digestive tract, blood vessel, heart, thymus, spleen, submandibular gland, peripheral blood, prostate, ovary, bone, joint, skeletal muscle and the like) or from cultures of these cells, or may be a synthetic protein.

Other cell membrane receptors include an ion channel-installed receptor (such as glutamate receptor in brain), and transporters includes those for transporting from a relatively low molecular substance such as glucose or amino acid to a relatively large molecule such as a protein or DNA.

A membrane binding enzyme may be any of various proteins involved in the intracellular signal transmission such as a G protein described above, and plays an important role with regard to cell growth regulation and cell carcinogenesis. Those also included in addition to these known membrane proteins are novel membrane proteins whose existence is expected from the genome information but whose functions are not understood yet. To produce these membrane protein in a state allowing correct three dimensional structures to be formed and to elucidate their functions serve to understand the functions of cells and organs of various organism and to provide an important means to develop a pharmaceutical related closely to such functions.

In another point of view, a membrane protein described above is characterized by its binding and interaction with a certain ligand upon expressing its physiological activity. A signal transducing pathway involves an important role played by a protein-protein interaction such as the interaction of the GPCR and a G protein in its regulatory function. On the other hand, a protein referred to as a transcription factor has a function for interacting with a DNA to regulate the expression of the gene. Otherwise, there are proteins interacting with peptides or amino acids or derivatives thereof or also with lower molecular substances such as metal ions, and the interaction with these ligands is important not only for the functional expression but also for the three dimensional structure maintenance of the protein. Accordingly, such a ligand binding protein is difficult to form a correct three dimensional structure when being expressed in the absence of its ligand and tends to undergo aggregation and be insolubilized. In a method according to the invention, such a ligand binding protein is also a target protein.

Accordingly, a "ligand" as used herein is a general term meaning substances binding specifically to proteins such as a substrate to be bound to an enzyme, co-enzyme or regulatory factor. Those also included are lectins, hormones, neurotransmitters and the like which bind to various receptors present in a cell membrane. Those which are applicable are not only low molecular weight molecules or ions but also high molecular weight substances.

(Construction of Polynucleotides for Expression)

A target protein described above is expressed as a fusion protein with thioredoxin in a cell-free protein synthesis system. A "fusion protein" or "fused protein" means a protein encoded by at least two, non-related fused genes or fragments thereof. Accordingly, a polynucoleotide encoding a fusion protein may contain, in addition to a thioredoxin gene, one or more of other genes or fragments thereof. A thioredoxin employed in the invention may not only be an E. coli thioredoxin (Lunn, C. A. et al., J. Biol. Chem. 259, 10469-10474 (1984)) but also a mammalian thioredoxin (Wollman, E. E. et al., J. Biol. Chem. 263, 15506-15512 (1988)), an yeast thioredoxin, a thioredoxin domain of a protein disulfide isomerase (Edman, J. C. et al., Nature 317, 267-270 (1985)) as well as a polypeptide formed as a result of deletion, addition or substitution of one or more amino acids in a polypeptide listed above which can catalyze the formation of a disulfide bond.

A polypeptide encoding any of these proteins or polypeptides (these terms have same meanings), is a nucleic acid polymer having a certain length consisting of ribonucleotides or deoxyribonucleotides. It is a single-stranded or double-stranded DNA or RNA. Moreover, it may be modified as known in the art, and may be labeled with a fluorescent substance, may be methylated, may be imparted with a cap structure, or may be substituted with a nucleotide analogue.

While a DNA is usually double-stranded, it may be cyclic double-stranded, or linear double-stranded, any of which can be transcribed and translated in a cell-free protein synthesis system. It can be produced by a conventional recombinant DNA technology well known in the art using E. coli and the like as a host. Alternatively, it can be prepared by a test tube DNA amplification technology such as a PCR without transforming a host cell. In the case of an RNA, a single-stranded mRNA is employed usually, and translated in a cell-free protein synthesis system. The technologies described above are discussed for example in Sambrook et al., Molecular Cloning: A Laboratory Manual Second Edition, 1989; D. N. Glover (ed.), DNA Cloning, Volumes I and II, 1985; M. J. Gait (ed), Oligonucleotide Synthesis, 1984.

A sequence required for transcription or translation in a cell-free protein synthesis system may for example be a potent promoter such as a T7 promoter, ribosome binding site, T7 terminator sequence as well as a tag sequence to be added for achieving an efficient purification of an expressed fused protein, such as histidine or GST.

Various methods can be employed for expressing a target protein as a fusion protein with a thioredoxin, including a method in which a target protein is fused at its N-terminal or C-terminal with a thioredoxin, or a thioredoxin sequence is inserted between domains constituting a target protein to allow a fusion protein to be expressed. A plasmid vector having multiple cloning sites near the thioredoxin sequence is employed preferably for producing a template DNA in a cell-free protein synthesis system by inserting an intended protein gene. Also since the target protein is purified by digesting limitedly from the fusion protein, it is especially preferred that a specific sequence capable of being cleaved by a protease such as an enterokinase is inserted in a boundary region between the thioredoxin and the target protein.

Also for an efficient expression, it is preferred that an operator sequence which controls the activity of a promoter is not contained, and if a commercially available E. coli expression vector is used, then a controlling sequence such as a lactose operator is removed.

As used herein, a "promoter" belongs to regulatory genes, and is a site where transcription of an operon is initiated upon binding with an RNA polymerase having a σ factor. An "operator" is also referred to as an operator gene, and is a repressor binding site and belongs to regulatory genes. It is present on one side of an operon between the RNA polymerase action site promoter and operon, or present as being overlapped partly with the promoter. When the repressor is bound to the operator, the transcription by the RNA polymerase is inhibited. A partial palindrome structure having 20 to 30 base pairs are usually comprised (for example, lactose operator).

(Expression in Cell-Free Protein Synthesis System)

A polynucleotide prepared as described above is expressed in a cell-free protein synthesis system. The cell-free protein synthesis system according to the invention is a system in which a protein is synthesized in a test tube using a cell extract solution, and such a system may be a cell-free translation system in which an information of an mRNA is read and a protein is synthesized on a ribosome, or a system involving both of a cell-free transcription system and a cell-free translation system in which a DNA is employed as a template to synthesize an RNA. When using a DNA as a template, an amplification reaction in a test tube such as a PCR allows a large number of template DNAs to be prepared simultaneously and rapidly without employing a complicated procedure such as a cloning required conventionally.

A cell extract solution mentioned above may be an extract solution from a eukaryotic or prokaryotic cell containing components required for synthesizing a protein, such as a ribosome and tRNA. Any known eukaryotic or prokaryotic cell can be employed, including E. coli, thermophilic bacteria, wheat germ, rabbit reticulocyte, mouse L cell, Ehrlich's ascitic cancer cell, HeLa cell, CHO cell and budding yeast and the like, with an E. coli-derived one (such as E. coli S30 cell extract solution) or highly thermophilic bacteria (Thermus thermophilus)-derived one being preferred for the purpose of obtaining a high synthetic yield. Such an E. coli S30 cell extract solution can be prepared from E. coli A19 (rna, met), BL21, BL21 star, BL21 codon plus strains and the like by a known method (see, Pratt, J. M. et al., Transcription and translation—a practical approach, (1984), pp. 179-209, Henes, B. D. and Higgins, S. J. ed., IRL Press, Oxford), or it may be any of commercially available ones supplied from Promega or Novagen.

While such a cell extract solution may be a concentrate of a cell extract solution mentioned above (hereinafter referred to as "concentrated cell extract solution") or a non-concentrated solution (hereinafter referred to as "crude cell extract solution"), a higher protein synthetic yield is achieved by using a concentrated cell extract solution. A method for obtaining such a concentrated cell extract solution is any known means such as an ultra filtration, dialysis, PEG precipitation and the like.

The composition of an inventive cell-free protein synthesis system comprises, in addition to a crude cell extract solution or concentrated cell extract solution derived for example from *E. coli* S30 (10 to 90% by weight), a DNA or RNA (such as mRNA) encoding a target protein, ATP (0.5 to 5 mM), GTP (0.005 to 1.0 mM), CTP (0.005 to 1.0 mM), UTP (0.005 to 1.0 mM), buffer solutions, salts, amino acids, RNase inhibitors, antibacterial agents, and if desired an RNA polymerase (when using a DNA as a template) and tRNA and the like. Otherwise, an ATP regenerating system, polyethylene glycol (for example PEG#8000), 3',5'-cAMP, folicacids (0.1 to 5 mM), reducing agents (for example dithiothreitol at 1 to 10 mM) may be contained.

A buffer solution may use a buffer such as Hepes-KOH, Tris-OAc and the like. Salts may be acetates (for example, ammonium salt, magnesium salt), glutamate and the like, while antibacterial agents may be sodium azide, ampicillin and the like. When using a DNA as a template, an RNA polymerase is added to a reaction system, which may be a commercially available enzyme such as a T7RNA polymerase.

In the invention, an ATP regenerating system may preferably be a combination of 0.02 to 5 µg/µl creatine kinase (CK) and 10 to 100 mM creatine phosphate (CP), to which it is not limited, and any known substance may be employed, such as a combination of 1 to 20 mM phosphoenol pyruvate (PEP) and 0.01 to 1 µg/µl pyruvate kinase and the like. Any of PK and CK is an enzyme which regenerates an ATP from an ADP, and requires PEP and CP as respective substrates.

In a preferred embodiment of the invention, a detergent is added to a cell-free protein synthesis system whereby further increasing the solubilizing rate of a fusion protein. Preferably, the detergent is selected appropriately based on the type of the target protein to be synthesized, and it may be any known substance as long as it causes no denaturation of the protein. An ordinarily employed detergent is grouped into any of nonionic, anionic and amphoteric detergents. The nonionic detergent includes digitonin, polyoxyethylene alkyl ether (Brij-based), polyoxyethylene sorbitan (Tween-based), β-dodecylmaltoside, β-octylglucoside, β-nonylglucoside, β-heptylthioglucoside, β-ocrylthioglucoside, scrose mono-decanoate, scrose mono-dodecanoate, octyltetraoxyethylene, octylpentaoxyethylene and dodecyloxtaoxyethylene and the like. The anionic detergent includes taurodeoxycholic acid and the like. The amphoteric detergent includes N,N-dimethyldecylamine-N-oxide, N,N-dimethyldodecylamine-N-oxide, N,N-dimethyldodecylammonio propanesulfonate and (3-[3-cholamidepropyl)-dimethylammonio]-1-propanesulfonate (CHAPS) and the like.

Any of these detergents may be employed alone or in combination of two or more. The amount of such a detergent is selected appropriately based on the type of the target protein, and the concentration used usually is preferably about 1 to 50 times the critical micelle concentration (CMC) of the relevant detergent, more preferably about 3 to 10 times. For example, when using as a detergent a nonionic detergent such as digitonin or Brij35, the concentration of digitonin is preferably 0.1 to 2.0% by volume, more preferably 0.4 to 1.5% by volume. The concentration of Brij35 is preferably 0.01 to 0.5% by volume, more preferably 0.02 to 0.2% by volume.

For analyzing the structure of a target protein produced by an inventive method or a domain thereof by an NMR method, it is preferred to prepare a sample labeled with $^{13}C/^{15}N$. Accordingly, for producing a protein labeled with $^{13}C/^{15}N$, a $^{13}C/^{15}N$-labeled algal amino acid mixture or 20 $^{13}C/^{15}N$-labeled amino acids may be employed instead of non-labeled amino acids in a cell-free protein synthesis system. A protein thus synthesized can be measured for $^{13}C/^{15}N$-HSQC spectrum. A combination of the labeling with a stable isotope which impart a deutrium to one methylene group of an amino acid specifically and the $^{13}C/^{15}N$-labeling is extremely suitable to an inventive method for producing in a cell-free protein synthesis system, since the consumption of a chemically synthesized stable isotope-labeled amino acid is reduced is as low as about ¹⁄₁₀₀ or less when compared with an expression in an *E. coli* cell, thus being extremely cost-effective.

On the other hand, for analyzing the structure of a target protein produced by an inventive method or a domain thereof by X-ray crystallography, an amino acid containing an atom exhibiting an abnormal scattering such as selenomethionine or selenocystaine is added to a cell-free protein synthesis system to synthesis a target protein. While in an expression method in a cell such as an *E. coli*, an amino acid metabolism or toxicity of selenomethionine may reduce the protein yield or reduce the substitution rate of selenomethylnine, an inventive cell-free protein synthesis system can avoid such an effect and enables the target protein synthesis at an extremely high substitution rate of 98% or higher. A heavy atom-substituted protein thus synthesized enables the collection of a complete data set only from one crystal by a multiple wavelength abnormal diffusion (MAD) method, whereby reducing the time period required for the three dimensional structure determination by an X-ray crystallography.

While an inventive cell-free protein synthesis system may employ any of known technologies in addition to a batch method, a flow method or dialysis method is preferred for the purpose of increasing the synthetic yield of a target protein. In such a method, it is possible to supplement a substrate during the synthetic reaction whereby prolonging the reaction duration, and a dialysis method enables an increase in the protein production from an equal amount of the cell extract solution usually by about 10 times when compared with a batch method. The productivity in an optimized cell-free protein synthesis system is far higher than the productivity in a cell such as an *E. coli* cell.

Also in the invention, a cell-free protein synthesis system is supplemented with a ligand which binds to a protein or a domain thereof, whereby increasing the amount of the protein synthesized and improving the solubilization rate. While such a ligand may vary depending on the target protein or a domain thereof, it may be one or more ligands selected from the group consisting of DNAS, RNAs, proteins, peptides, amino acids, lipids, saccharides and derivatives thereof, alkaloids, terpenes, coenzymes and metal ions. As a result of the binding to such a ligand, the three dimensional structure of the target protein is stabilized and the decomposition is suppressed, while a correct three dimensional structure can be formed, whereby possibly suppressing the insolubilization or aggregation.

Accordingly, in one embodiment of the invention, a method for producing a target protein as a fused protein with a thioredoxin in a cell-free protein synthesis system wherein a ligand binding to the target protein described above is added to this cell-free protein synthesis system described above is provided.

The level of the target protein expressed can be measured by various methods. An SDS polyacrylamide gel electrophoresis (SDS-PAGE) is the most common analytical method. When a protein is treated with the SDS under a reducing condition, the protein is completely denatured, and cleaved into polypeptides. The polypeptides bind to the SDS in an amount about 1.4 times by weight under the reducing condition to form an SDS complex. The SDS complex thus formed runs at a constant speed in a constant electric field due to the negative charge of the excessive dodecyl sulfate ion. Accordingly, an electrophoresis on an SDS-containing polyacrylamide gel enables the separation of the proteins based on the molecular weight as a result of the molecular sieve effect, whereby detecting the target protein using the molecular weight as an index. The SDS-PAGE is classified into a continuous buffer solution system employing a buffer solution at a single pH and a non-continuous buffer solution system employing buffer solutions at different pHs. Also on the basis of the type of the proteins to be separated, a low N,N'-methylenebisacrylamide (BIS) level gel electrophoresis, gradient gel electrophoresis and tricine-SDS-PAGE may also be employed. A protein thus separated can be quantified usually by staining with a dye such as Coomassie blue. A silver staining method enables the identification of a protein at a sensitivity 20 to 100 times that by the Coomassie blue staining method. Alternatively, a commercially available fluorescent reagent such as SYPRO Ruby or SYPRO Orange can be employed to achieve a highly sensitive detection on a gel (Patton, W. F. Electrophoresis, 21, 1123-1144(2000)). The detection can be accomplished also by an autoradiography employing a radioactively labeled protein or by a fluorography.

(Purification of Expressed Protein and Evaluation of Biological Activity)

The purification of a synthesized fusion protein can be conducted somewhat easily since there are extremely reduced number of types and amounts of contaminants when compared with the separation from a viable cell. The purification may employ, depending on the nature of the protein, any of known procedures alone or in combination as appropriate. For example, customary methods such as ammonium sulfate or acetone precipitation, acid extraction, anion or cation exchange chromatography, hydrophobic interaction chromatography, affinity chromatography, gel filtration chromatography, high-performance liquid chromatography (HPLC), extraction from an electrophoresis gel, chromatofocusing and the like may be mentioned.

In a preferred embodiment of the invention, a specific sequence cleaved by a protease is inserted within a thioredoxin and a target protein, and an enzyme which digests this specific sequence limitedly is reacted to purify the target protein exclusively from the fusion protein. Such a limitedly digested enzyme may be any of various enzymes, such as thrombin, Factor Xa, enterokinase and the like.

Also for the purpose of analyzing the in vivo structure and functions of a membrane protein and the like more correctly, it is preferred to reconstitute a protein synthesized in a cell-free protein synthesis system into an artificial membrane or liposome. In a first method of such a reconstitution, the concentration of a detergent is reduced simultaneously with or at a certain time point after the synthetic reaction in a cell-free protein synthesis system supplemented with the detergent and a lipid whereby reconstituting the synthesized protein into a liposome (lipid vesicle). As used herein, the reconstitution means a reconstitution of a system analogous to an in vivo state by embedding at least a part of the synthesized membrane protein in a liposome consisting of a double layer or multiple layer formed from a lipid. The lipid which can be employed in this method may for example be a simple lipid such as an acylglycerol (neutral fat) or cholesterol ester as well as a composite lipid such as a phospholipid and glycolipid. The phospholipid includes phosphatidylcholine (PC), phosphatidylethanolamine (PE), phosphatidylserine (PS), phosphatidylinositol (PI), phosphatidylglycerol (PG), plasmalogen, sphyngomyelin, ceramideciliatin and derivatives thereof, while the glycolipid may for example be a sphyngoglycolipid which is a generic name including cerebroside, globoside, ganglioside. Any of these substances may be employed alone or in combination of two or more, in an amount which may be selected appropriately based on the lipid employed, and is usually about 0.1 to 10 mM.

In the second method, a thioredoxin-fused membrane protein synthesized in a cell-free protein synthesis system is recovered and purified for example by means of a filtration or centrifugation, and then mixed with a detergent and a liposome, and then the concentration of the detergent is reduced, whereby preparing a complex of an intended thioredoxin-fused membrane protein with the liposome. The detergent to be added after the protein synthesis reaction may be any detergent as long as it can solubilize the synthesized thioredoxin-fused membrane protein and can inhibit the aggregation, and is not limited to a mild detergent. Those employed preferably are N-lauryl sarcosine, N-dodecyl-β-D-maltoside and the like.

Alternatively, these first and second methods can be combined in a more preferred manner. Such a thioredoxin-fused membrane protein synthesized in the presence of a lipid and a liposome and/or mixed with a liposome after the synthesis, or a membrane protein obtained by the limited digestion of the thioredoxin moiety of this fused protein using an enterokinase and the like is reconstituted as being integrated into the double layer or multiple layer of the lipid upon formation thereof by reducing the concentration of the detergent. In order to reduce the concentration of the detergent, a dialysis method, a dilution method or a method employing addition of an adsorbent for the detergent may be contemplated.

As used herein, a "liposome (lipid vesicle)" means a double layered vesicle formed as a result of a spontaneous agglomeration of a lipid mentioned above in an aqueous solution, and can readily be prepared by a method known in the art. For example, an aqueous solution is added to a thin film of a lipid, stirred and the particle size is adjusted as desired. While the nature of a liposome may vary depending on the composition of the lipid (cationic, anionic or neutral lipid species), an identical method can be used for the preparation regardless of the type of the lipid. Firstly in the case of two or more lipid constituents, these lipids are mixed thoroughly in an organic solvent. Then the organic solvent is distilled off to form a lipid membrane. Subsequently, an aqueous solution is added to the dried lipid film, and then stirred. The temperature of the aqueous solution is preferably higher than the gel-liquid crystal transition temperature of the relevant lipid. The liposome thus formed is a large multilayer vesicle (LMV), and the respective lipid double layers (bilayer) are insulated from each other by a water layer. Once a stable LMV is formed, its particle size can be reduced as desired by various methods such as an ultrasonication or mechanical treatment.

In the invention, a liposome to be added during or after a cell-free protein synthesis reaction is preferably a unilaminar vesicle (UV) having a uniform particle size. By adjusting the conditions of the ultrasonication or mechanical treatment described above, those skilled in the art can impart a uniform particle size readily to a liposome. For example, by conducting an ultrasonication, a small unilaminar vesicle (SUV) whose particle size is within the range from 15 to 50 nm is usually formed. An ultrasonication machine fitted with a probe tip or cup horn is employed usually. On the other hand, a method employing an extruder is known as a mechanical treatment method (for example, Mini-Extruder from Avanti). In this extrusion method, a lipid suspension is passed mechanically through a polycarbonate filter having a certain pore size to prepare a liposome whose particle size is close to the pore size of the filter employed. Before passing through the filter of the final pore size, it is preferable that the LMV suspension is subjected to a freezing and thawing process or is passed through a filter having a larger pore size. Similarly to the ultrsonication, it is preferable that the temperature at which the extruder is operated is the gel-liquid crystal transition temperature of the relevant lipid or higher. The particle size of the liposome prepared by the extruder varies depending on the number of filter passage times. At an early stage of the extrusion process (first 2 to 3 passages), two peaks are observed in the particle size distribution corresponding to the original-sized LMV and the desired-sized liposome, but after sufficient number of the filter passage times, a liposome having a monophasic particle size distribution can be obtained. For example, when using a filter whose pore size is 100 nm, a large unilaminar vesicle (LUV) whose particle size is 120 to 140 nm is generally obtained.

The particle size of a liposome employed in the invention is preferably within the range from 50 to 200 nm. Such a particle size can be determined by a photon correlation method (also referred to as light scattering method; Particle Size Analysis-Photon Correlation Spectroscopy, ISO 13321), zeta potential measurement method, electrical measurement method (using Coulter counter and the like) or ultracentrifugation method and the like.

Alternatively, in a different embodiment of the invention, for the purpose of suppressing denaturation of a thioredoxin-fused membrane protein by a detergent as far as possible, the dialysis method described above is replaced by a freezing/thawing/ultrasonication method (freeze-thaw-sonication procedure), repetitive hydrophobic chromatography to remove the detergent (cyclic detergent removal procedure) (see, Palmieri, F., Indiveri, C., Bisacchia, F. and Iacobazzi, V., Methods Enzymol 260, 349-369 (1995)). In the freezing/thawing/ultrasonication method, a protein dissolved in a detergent is mixed with a liposome, and then cooled rapidly for example by using a liquid nitrogen, followed by thawing at 15 to 20° C., followed by an ultrasonication for a short period. A slow thawing allows the protein to be inserted into a void opened in the liposome membrane as a result of the rapid cooling, and the void in the liposome is closed as a result of a very short time ultrasonication. On the other hand, the repetitive hydrophobic chromatography involves a repetitive passage of a detergent, protein and phospholipid through a column packed for example with Amberlite XAD-2 to remove the detergent, whereby forming a protein-liposome complex. It is assumed that since the hydrophobic resin adsorbs the nonionic detergent selectively, the remaining phospholipid and the protein form a double molecular layer.

A complex of a thioredoxin-fused membrane protein and a liposome having a uniform particle size produced by a method according to the invention can be employed for analyzing the three dimensional structure after crystallization and also for screening for a ligand which binds to this membrane protein after immobilizing onto a glass substrate or a well of a microtiter plate.

EXAMPLES

The results of the investigation of the methods according to the present invention are explained in more detailed by the following examples using cDNA fragments encoding rat neurotensin receptor (NTR), human muscarinic acetylcholine receptor m2 subtype (m2) and human β2-adrenergic receptor (β2AR-Gs), however, the present invention is not limited to these examples. Unless otherwise specified, % is % by volume.

Example 1

Synthesis of Rat Neurotensin Receptor (NTR)

NTR is a member of G protein-coupled receptor family, and when binding to its ligand neurotensin, it activate a phospholipase C via G protein to produce inositol-1,4,5-trisphosphoric acid/diacylglycerol. In this example, various recombinant vectors expressing the thioredoxin-fused NTR were prepared, and examined for the expression levels in a cell-free protein synthesis system. No fusion with the thioredoxin served as a control.

(1) Preparation of Plasmid for NTR Expression

Using the NTR cDNA-containing vector, pRG/III-hs-MBP-T43NTR-TrxA-H 10 (see, Grisshammer, R. et al., Biochemical Society Transactions, 27, 899-903 (1999)) as a template, PCR was conducted to amplify the NTR cDNA together with two primers. A cDNA fragment amplified using the 5' primer: 5'-CACCATGACCTCGGAATCCGA-CACGGCAGGGCCCAAC-3'(SEQ ID No. 1) and the 3' primer: 5'-GTACAGGGTCTCCCGGGTGG-3'(SEQ ID No. 2) contained a coding region from the 43rd amino acid to the C-terminal amino acid of the NTR containing the initiation codon methionin (MT43NTR). On the other hand, a cDNA amplified using the 5' primer: 5'-CACCAT-GAAAATAAAAACAGGTGCACGCATCC-3'(SEQ ID No. 3) and the 3'primer: 5'-GTACAGGGTCTCCCGGGTGG-3' (SEQ ID No. 2) encoded a polypeptide from the 43rd amino acid to the C-terminal amino acid of the NTR linked downstream of an E.coli maltose-binding protein (MBP) (MBP-T43NTR). Each of these two cDNAs was cloned into a vector pET102/D-TOPO (Invitrogen) for expressing a fusion protein with the thioredoxin, and each expression plasmid was prepared. Similarly, each of these cDNA fragments was cloned also into a pET101/D-TOPO (Invitrogen) expressing a protein which was not fused with the thioredoxin, which was employed as a control.

(2) Synthesis of Thioredoxin-Fused NTR in Cell-Free Protein Synthesis System

The E. coli S30 extract solution was prepared from E. coli BL21 Star (DE3) strain according to the method by Zubay et al (Annu. Rev. Geneti., 7, 267-287, 1973). The protein synthesis reaction employed a solution having the composition indicated in Table 1 shown below, to which L-[$^{14}$C]

leucine and each of various expression plasmids described above at concentrations varying from 1 to 20 μg/ml were added. A reaction solution having the same composition but also containing 0.2% as a final concentration of digitonin (WAKO PURE CHEMICAL) was also prepared. The protein synthesis reaction was carried out by a batch method for 1 hour at 37° C. in 30 μl as a final volume of a reaction solution containing 7.2 μl of the *E. coli* S30 extraction solution.

TABLE 1

| Composition | Concentration |
|---|---|
| HEPES-KOH pH 7.5 | 58.0 mM |
| Dithiothreitol | 2.3 mM |
| ATP | 1.2 mM |
| CTP, GTP, UTP | each 0.9 mM |
| Creatine phosphate | 81.0 mM |
| Creatine kinase | 250.0 μg/ml |
| Polyethylene glycol 8000 | 4.00% |
| 3',5'-cAMP | 0.64 mM |
| L-(−)-5-formyl-5,6,7,8-tetrahydrofolic acid | 35.0 μg/ml |
| *E. coli* total tRNA | 170.0 μg/ml |
| Potassium glutamate | 200.0 mM |
| Ammonium acetate | 27.7 mM |
| Magnesium acetate | 10.7 mM |
| Amino acid (20 types) | each 1.0 mM |
| T7RNA Polymerase | 16.0 units/μl |
| Template DNA | 1–20 μg/ml |

(3) Measurement of Expression Level

Figure 2:
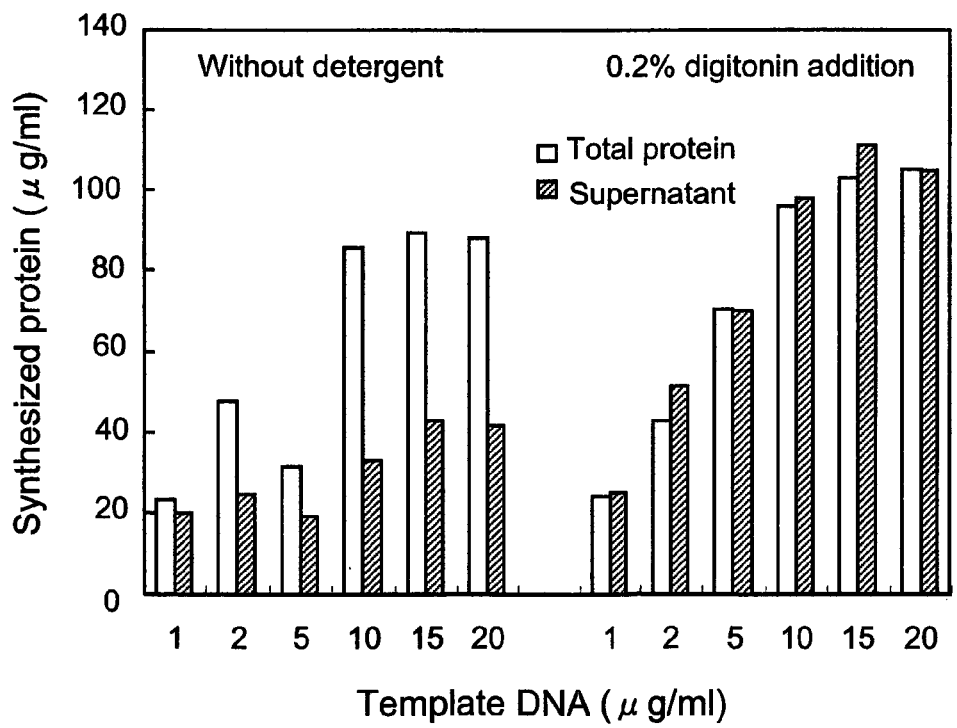
FIG. 2 shows the results of the expression of thioredoxin fused MT43-NTR in a cell-free protein synthesis system by a batch method according to the present invention.
Figure 3:
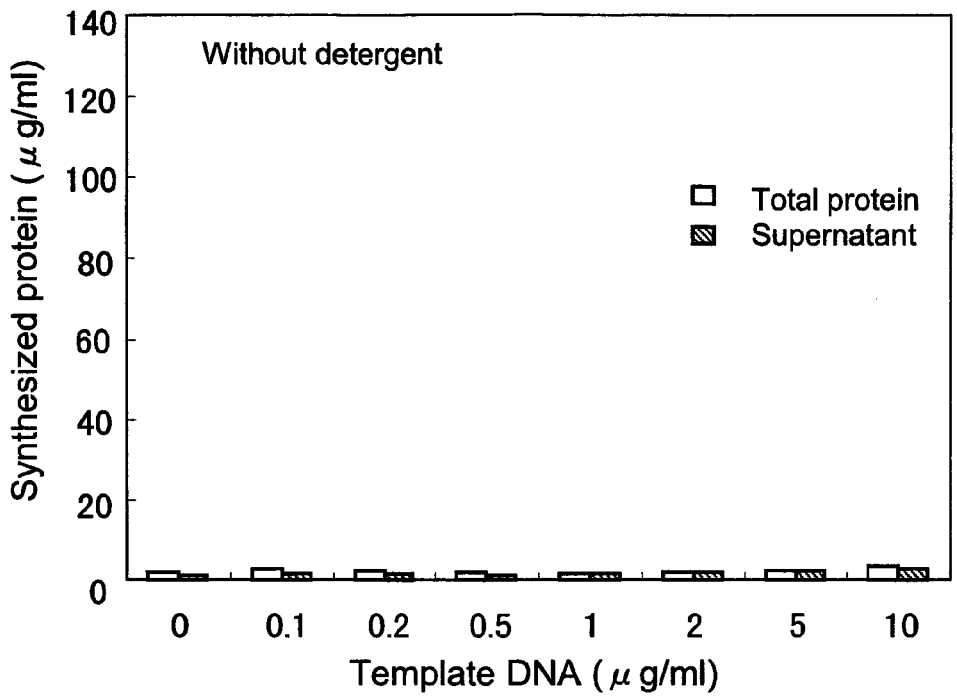
FIG. 3 shows the results of the expression of MBP-T43NTR in a cell-free protein synthesis system by a batch method.
Figure 4:
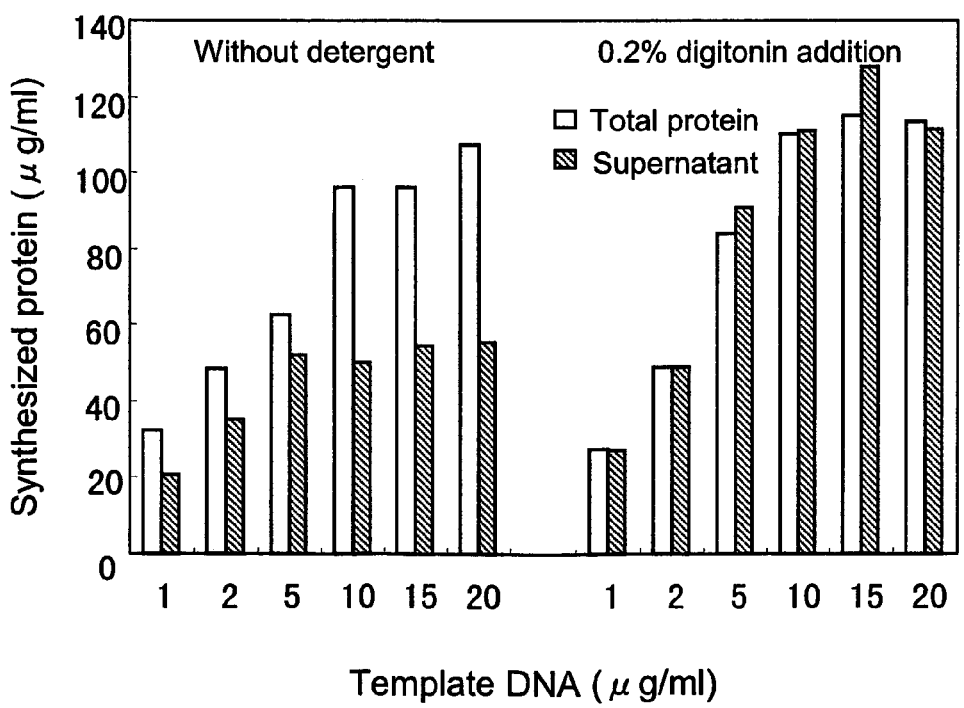
FIG. 4 shows the results of the expression of thioredoxin fused MBP-T43NTR in a cell-free protein synthesis system by a batch method.

After completion of the synthesis reaction, a 5 μl aliquot was taken from the resultant synthesis reaction solution, and the radioactivity of the entire labeled protein (total protein) contained in the insoluble fraction and the supernatant was measured using TOP COUNT (Packard). Then, the remaining 25 μl of the reaction solution was centrifuged at 3,000×g for 10 minutes and a 5 μl aliquot of the supernatant was taken and examined for the radioactivity similarly. The protein concentration (μg/ml) was obtained by multiplying the coefficient per unit radioactivity calculated previously from the number of leucine molecules and the like in the target protein. The results are shown in FIGS. 1 to 4. FIG. 1 shows the results of the expression only of MT43-NTR without fusion with the thioredoxin. Regardless of the amount of the template DNA employed or the addition of the detergent, almost no expression of the protein was observed under any condition. On the contrary, the fusion with the thioredoxin resulted in an increase in the fused protein expression in response to the increase in the template DNA as shown in FIG. 2. Especially under the condition in the presence of 0.2% digitonin, most of the protein was found in the supernatant fraction. Similarly, the NTR fused with the *E. coli* MBP exhibited almost no expression as shown in FIG. 3, but this MBP-T43NTR fused further with the thioredoxin resulted in the expression of the fusion protein in a large amount as shown in FIG. 4. Also in this case, the addition of 0.2% digitonin resulted in most of the protein found in the supernatant fraction. Based on these results, it was revealed that the fused protein of the thioredoxin with the NTR can be synthesized in a large amount and in a readily solubilizable state in the cell-free protein synthesis system. Also based on the results of the expression only of the MBP-T43NTR, a fusion merely with other proteins led to a low level expression, indicating that the fusion with the thioredoxin gives the inventive advantage.

Example 2

Synthesis of Human Muscarinic Acetylcholine Receptor m2 Subtype (m2)

The m2 is a member of G protein-coupled receptor family and is a receptor which is expressed mainly from peripheral tissues including heart and intestine (smoothmuscle) to central nervous system. The nucleotide sequence of its cDNA is known, and the gene expression has been tried in an expression system of baculovirus and the like (Hayashi, M. K. and Haga T., J. Biochem 120, 1232-1238 (1996)). In this example, a human m2 cDNA provided by Prof. Dr. Haga in Tokyo University (previous report) was employed as a template together with 5' primer: 5'-CACCATGGAT-GACTCCACGGACTCCT-3' (SEQ ID No. 4) and 3' primer: 5'-CCTTGTAGCGCCTATGTTCTTATAATGACA-3' (SEQ ID No. 5) to examine the expression level in the cell-free protein synthesis system by the method similar to that in Example 1.

Figure 5:
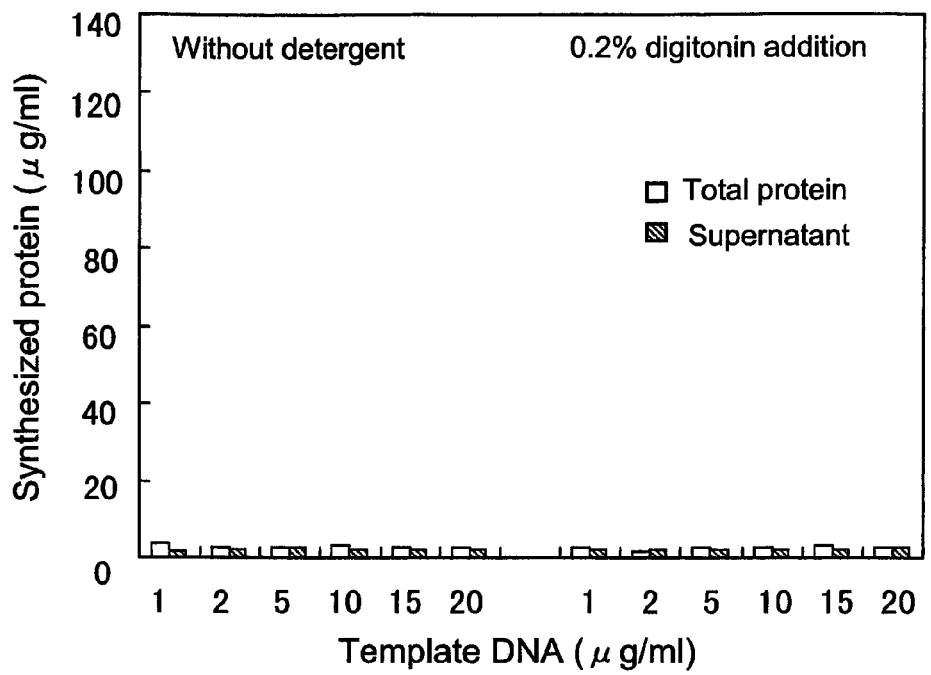
FIG. 5 shows the results of the expression of m2 in a cell-free protein synthesis system by a batch method.
Figure 6:
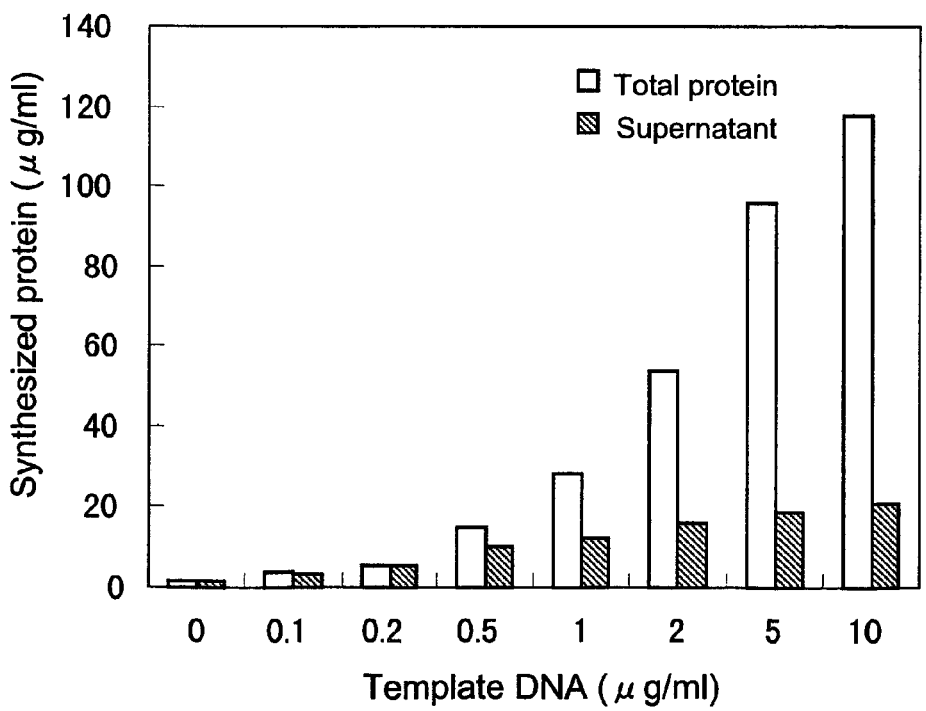
FIG. 6 shows the results of the expression of thioredoxin fused m2 in a cell-free protein synthesis system by a batch method.
Figure 7:
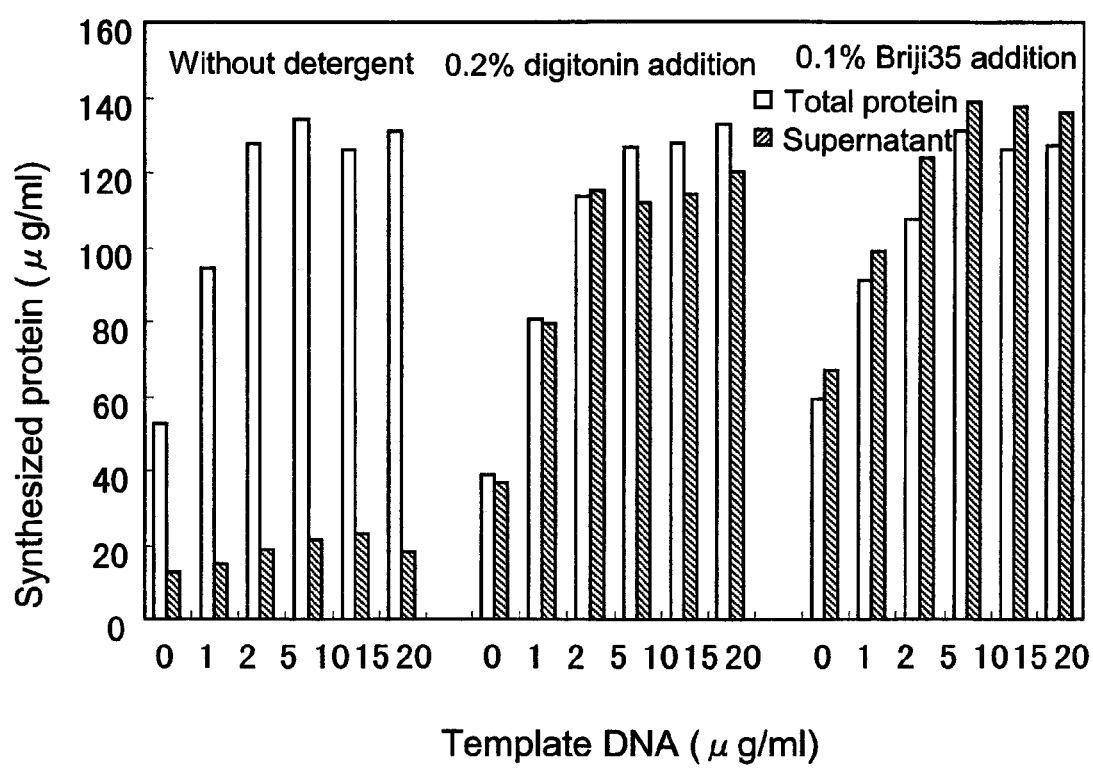
FIG. 7 shows the results of the expression of thioredoxin fused m2 in a cell-free protein synthesis system by a batch method in the presence of 0.2% digitonin or 0.1% Brij35.

The results are shown in FIGS. 5 to 7. As shown in FIG. 5, the expression only of the m2 after cloning into a pET101/D-TOPO as a control resulted in almost no expression regardless of the addition of the detergent. On the other hand, the expression of the fusion protein with the thioredoxin after cloning into a pET102/D-TOPO resulted in the expression which was dependent on the amount of the template DNA added as shown in FIG. 6. FIG. 7 shows the results of the addition of 0.2% digitonin or 0.1% Brij35, which revealed that most of the protein migrated into the supernatant similarly to Example 1 and a large amount of the protein was expressed in an extremely highly soluble state.

Example 3

Synthesis of β2-Adrenergic Receptor (β2AR)

The β2AR is a member of G protein-coupled receptor family, and when binding to its ligand, adrenaline, it activates adenylyl cyclase via stimulatory G protein to serve to increase the intracellular cyclic AMP (cAMP) concentration. This protein is known, and the nucleotide sequence of its cDNA was deposited to GenBank (Accession Number AF022956). In this example, in order to increase the expression efficiency of a fused protein of this β2AR with the thioredoxin, three vectors were prepared and cloned with a β2AR-encoding DNA to effect the expression in the cell-free protein synthesis system by the batch method, whereby examining the thioredoxin-fused protein expression level. Then, β2AR-Gs was expressed in a large amount in the cell-free protein synthesis system by the dialysis method, and the synthesized β2AR-Gs was reconstructed to assess the ability of binding to the ligand.

(1) Thioredoxin-Fused Expression Vector Construction

The plasmid pFASTBAC-β2AR-Gs-H6 containing a fusion gene of human β2-adrenergic receptor and stimulatory G protein (Gs) was provided by Prof. Dr. Robert J. Lefkowitz in Duke University Medical Center (Kobilka, B. K. et al., Proc. Natl. Acad. Sci. USA, 84, 46-50 (1987)). Using this plasmid as a template together with a common forward primer: 5'-CACCATGGGGCAACCCGGGAACG-GCA-3' (SEQ ID No. 6) and a reverse primer for the β2AR-Gs: 5'-TGGAGGCAGTCATACTCGACGAG-3' (SEQ ID No. 7) and a reverse primer for the β2AR: 5'-CCTTAACATCATGTTTACTGAGTGACGAC-3' (SEQ ID No. 8), a PCR was conducted to amplify the cDNA fragments of β2AR fused with stimulatory G protein (β2AR-Gs) and of the β2AR alone. Each of these cDNA fragments was cloned into a vector pET102/D-TOPO or pET101/D-TOPO (Invitrogen) for the expression of the thioredoxin-fused or non-fused protein, respectively, to prepare 4 expression plasmids (β2AR/102, β2AR-Gs/102, β2AR/101 and β2AR-Gs/101) (see FIG. 8).

In order to increase the expression efficiency of the thioredoxin-fused protein, a vector formed by introducing multiple cloning sites of 9 restriction enzymes (HpaI, EcoRI, SalI, KpnI, NcoI, SpeI, PmaCI, NotI, XhoI) after the thioredoxin sequence of the commercially available pET102/D-TOPO (referred to as MCS) was prepared, and from this vector, a vector having deletion of the lactose operator sequence (lacO) was prepared (referred to as MCS-ΔlacO) and also a vector having deletion of a V5 epitope and 6 histidine sequence from the MCS (referred to as MCS-ΔVH) was prepared. Typically, a restriction enzyme cleavage site-encoding oligonucleotide: 5'-GTTAACGAATTCGTCGACGGTACCCCATGGACTAGTCACGTGCGGCCGCTCGAG-3' (SEQ ID No. 9) was synthesized, and cloned into the pET102/D-TOPO to prepare a vector MCS (6369 bp) having multiple cloning sites. Then, the 23 base-pair lactose operator sequence was replaced with the 17 base-pair sequence: 5'-GAGACCACAACGGTTTC-3' (SEQ ID No. 10) using a QuickChange Site-Directed Mutagenesis Kit (STRATAGENE). The MCS-ΔVH (6279 bp) having deletion of a V5 epitope and 6 histidine sequence from the MCS was also prepared similarly using the QuickChange Site-Directed Mutagenesis Kit (STRATAGENE). Into these vectors, the β2ARcDNA was inserted to prepare the plasmids for the expression. Thus, using the pFAST-BAC-β2AR-Gs-H6 as a template, together with a 5' primer: 5'-GAGAATTCATGGGGCAACCCGGGAACGG-3' (SEQ ID No. 11) and a 3' primer: 5'-CTCTCGAGCAGCAGTGAGTCATTTGTAC-3' (SEQ ID No. 12), a PCR was conducted to amplify the β2ARcDNA fragment. This cDNA fragment was cleaved with restriction enzymes EcoRI and XhoI, cloned into the multiple cloning sites of three vectors described above to construct the plasmids for the expression in the cell-free protein synthesis system (see FIG. 8). The respective expression vector were designated as β2AR/MCS, β2AR/MCS-ΔlacO and β2AR/MCS-ΔVH.

(2) Comparison of Protein Synthesis Rate by Batch Method

Figure 8:
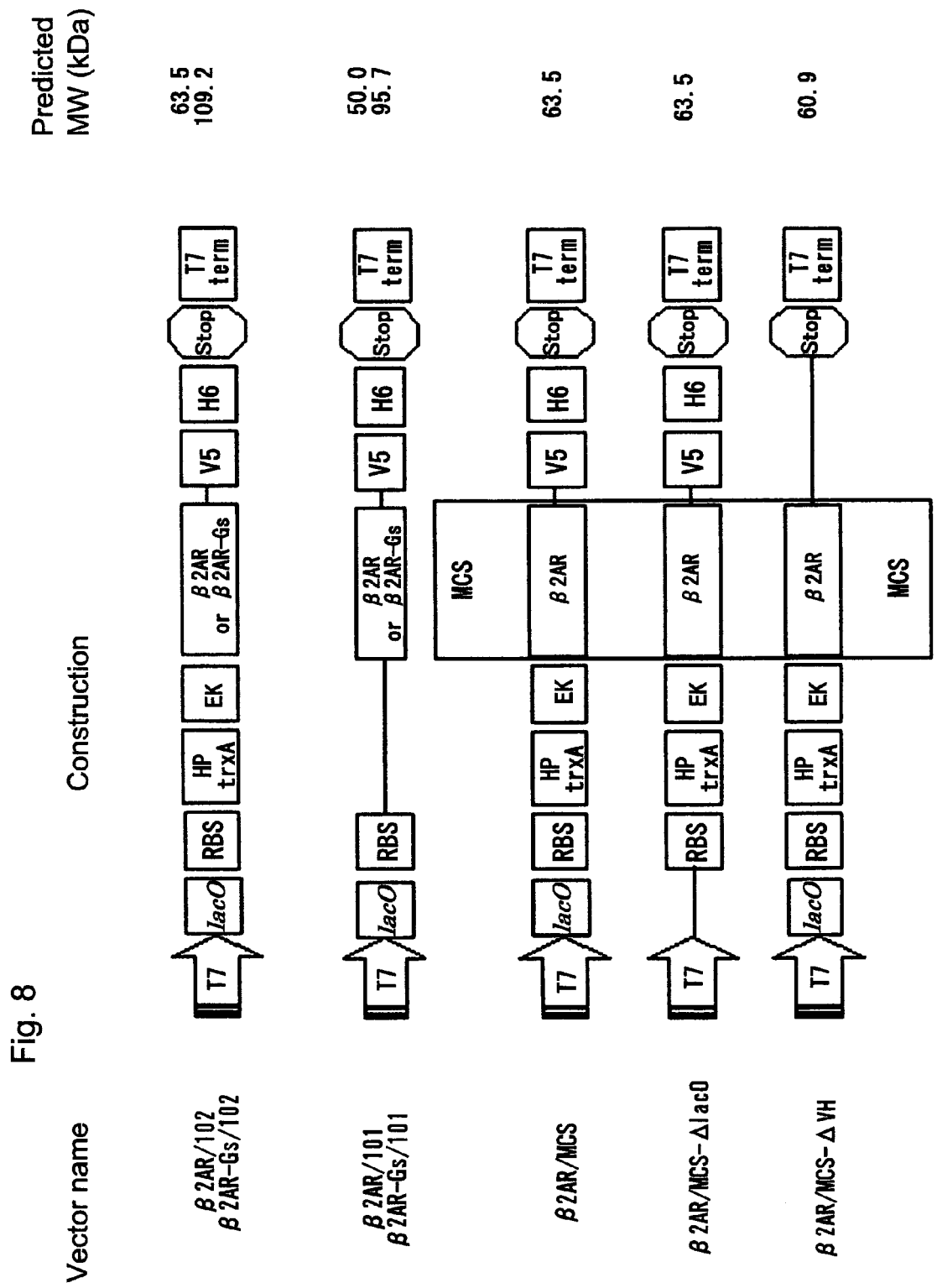
FIG. 8 shows construction of the thioredoxins-fused human β2 adrenergic receptor expression vectors. In the figure, β2AR denotes human β2-adrenergic receptor; β2AR-Gs denotes G protein Gs-fused human β2-adrenergic receptor; T7 denotes T7 promoter; LacO denotes lactose operator; RBS denotes ribosome binding site; HPtrxA denotes histidine patched thioredoxin A; BK denotes enterokinase cutting site; V5 denotes V5 domain derived from the P and V protein of paramyxovirus, SV5; H6 denotes hexa-histidine; Stop denotes stop codon; T7 term denotes T7 terminator; MCS denotes multi-cloning sites including the cleavage site for nine restriction enzymes (HpaI, EcoRI, SaiI, KpnI, Ned, SpeI, PmaCI, NotI, and XhoI).
Figure 9A:
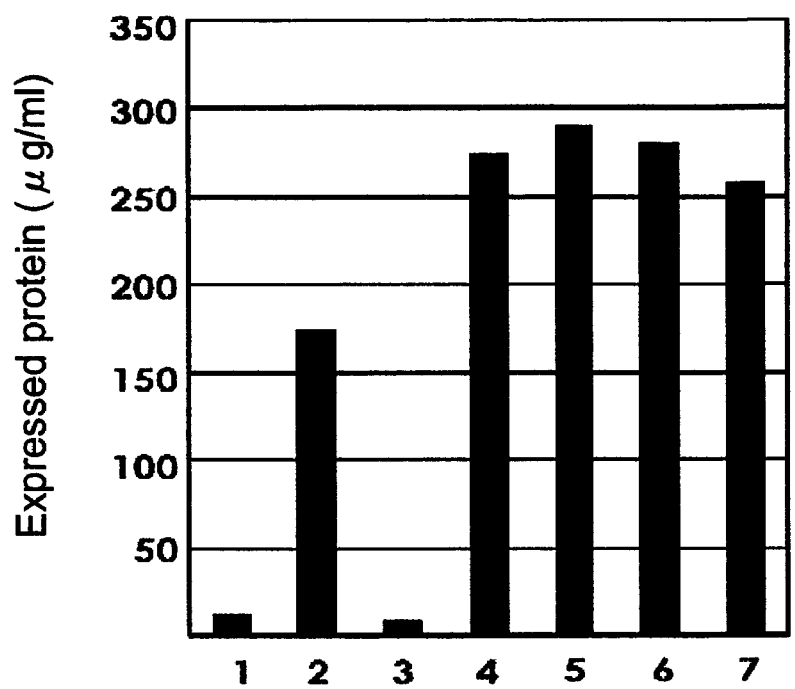
FIG. 9A shows the level of the protein per ml of the synthesis reaction mixture calculated from the radioactivity of the labeled protein.
Figure 9B:
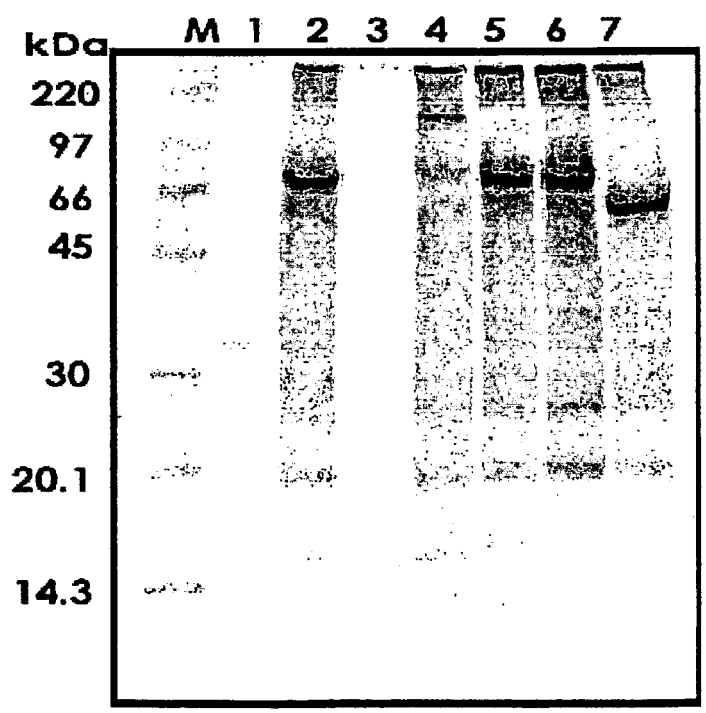
FIG. 9B shows the results of the detection of each sample by autoradiography after separation by SDS-PAGE.

By the method similar to that in Example 1, the *E. coli* S30 extract solution and the 7 expression vectors shown in FIG. 8 were used to synthesize β2AR proteins. To a solution having the composition shown in Table 1, 0.46 mM of L-[$^{14}$C]leucine (220 to 300 mCi/mmol, Moravek) and various expression plasmids at 10 μg/ml were added. The protein synthesis reaction was conducted for 1 hour at 37° C. in 30 μl as a total volume of a reaction solution containing 7.2 μl of the *E. coli* S30 extraction solution. The results are shown in FIG. 9A and FIG. 9B. FIG. 9A shows a value of the total synthesized protein per ml of the reaction solution which was calculated from the labeled radioactivity. FIG. 9B shows the results of the procedure in which the sample after the synthesis reaction was separated by SDS-PAGE using a polyacrylamide gel for electrophoresis containing a gradient of acrylamide concentration from 10% to 20% (MULTIGEL 10/20™, Daiichi Pure Chemicals Co., Ltd., and then the gel was dried and brought into a close contact with an Imaging Plate (BAS-SR2040, Fuji Film), which was allowed to stand for 24 hours in a dark place, and then subjected to an autoradiography using a bioimaging analyzer BAS2500 (Fuji Film) whereby detecting the labeled proteins. Lane 1 represents the results when using as a template DNA the β2AR/101, Lane 2 using β2AR/102, Lane 3 using β2AR-Gs/101, Lane 4 using β2AR-Gs/102, Lane 5 using β2AR/MCS, Lane 6 using β2AR/MCS-ΔlacO and Lane 7 using β2AR/MCS-ΔVH. Based on the results shown in FIG. 9A and FIG. 9B, almost no expression of the proteins which had not been fused with the thioredoxin (Lanes 1 and 3) was observed, but the fusion with the thioredoxin resulted in a marked increase in the expression level (Lanes 2 and 4 to 7). As evident from Fig. 9B, the apparent molecular weights of these proteins were 64 kDa (Lanes 2, 5 and 6), 109 kDa (Lane 4) and 61 kDa (Lane 7), which were almost in agreement with the expected values. Also as evident from FIG. 9A, the synthesis reaction only for 1 hour using 30 μl of the reaction solution resulted in the synthesis of the protein in an amount as large as about 150 to 250 μml.

Figure 10A:
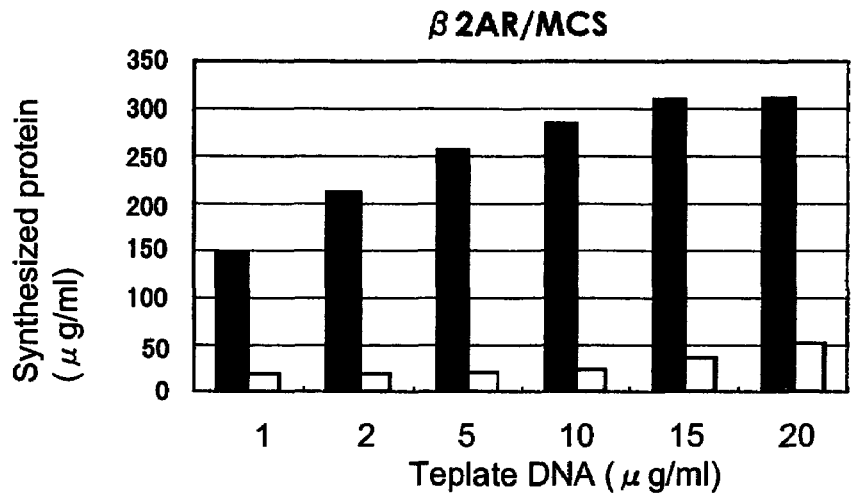
FIG. 10 A-C shows the results of the synthesis of the β2AR cloned into any of three expression vectors in a cell-freeprotein synthesis system by a batch method using various template DNA levels.
Figure 10B:
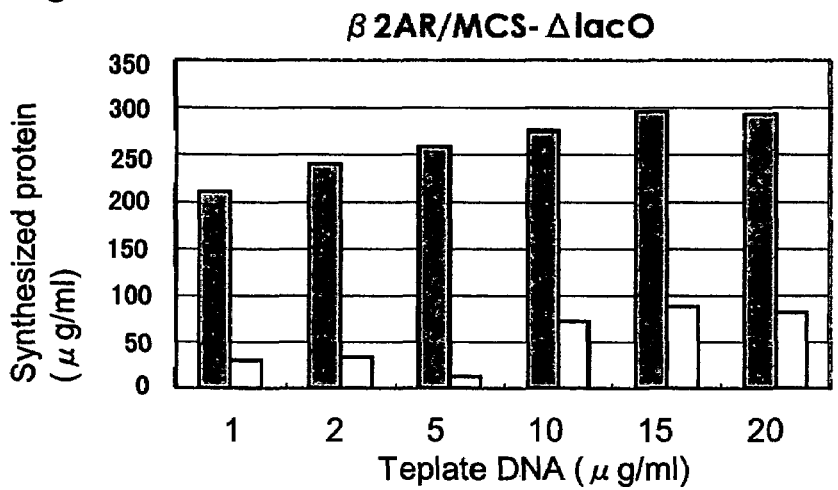
Figure 10C:
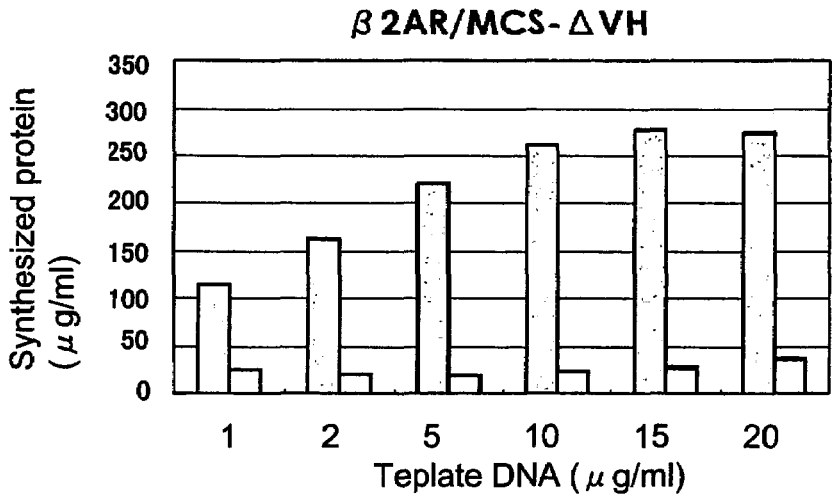

Then, using three expression vectors β2AR/MCS, β2AR/MCS-ΔlacO and β2AR/MCS-ΔVH, the synthesis reaction was conducted using different amounts of the template DNA. The results are shown in FIG. 10 A-C. As shown in FIG. 10B, the β2AR/MCS-ΔlacO exhibited the fused protein synthesis regardless of the amount of the template DNA added, and was sufficient even with 1 μg/ml addition. When using other plasmids as template, the protein synthesis level was increased dependently on the template DNA amount within the lower concentration region (FIG. 10A and FIG. 10C). Based on these results, the template DNA having the deletion of the lactose operate is extremely excellent in terms of the expression efficiency in the cell-free protein synthesis system by the method of the invention.

(3) Effect of Detergent on β2AR

Figure 11A:
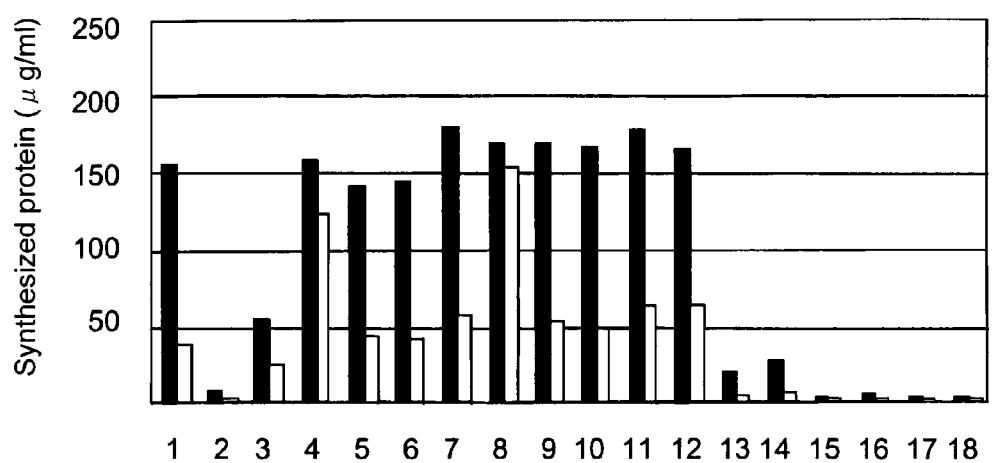
FIG. 11A shows the results of the investigation of the effects of 18 detergents in a cell-free protein synthesis system by a batch method.
Figure 11B:
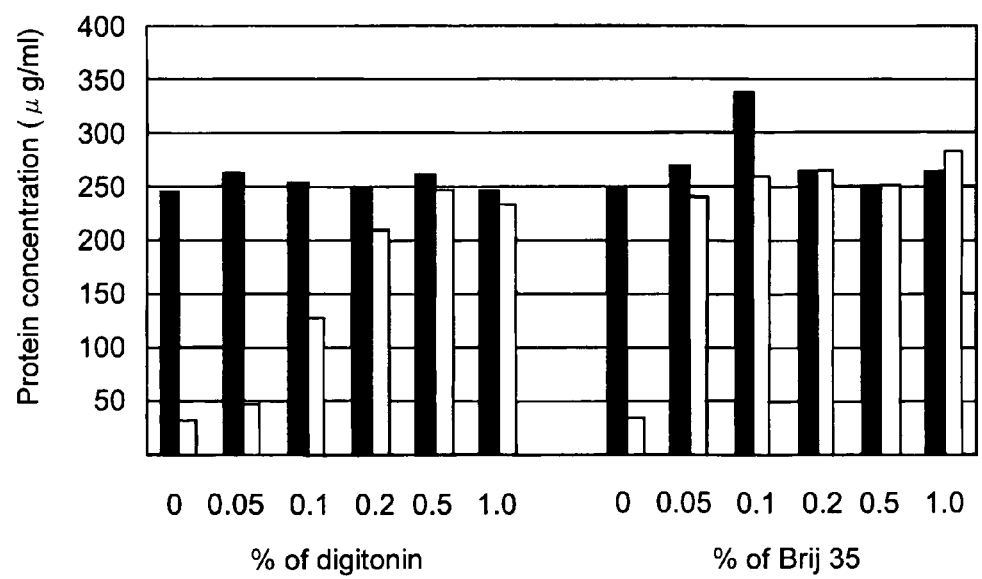
FIG. 11 A-B shows the effects of the addition of various detergents on the synthesis level and the solubility of the β2AR-GS.

Using the *E. coli* S30 extraction solution, β2AR proteins were synthesized by the method similar to that in Example 1. To the solution having the composition indicated in Table 1, L-[$^{14}$C] leucine and the β2AR-Gs/102 at 10 μg/ml were added. The protein synthesis reaction was conducted for 1 hour at 37° C. in 30 μl as a total volume of a reaction solution containing 7.2 μl of the *E. coli* S30 extraction solution. FIG. 11A shows the results of the investigation of the effect on the expression and the solubilization of the β2AR protein when using 18 detergents. A solid bar represents a total protein synthesized per ml of the reaction solution, while an open bar represents a supernatant protein level. Lane 1 was obtained using pure water as a control, Lane 2 using N-octyl-β-D-glucoside (OG), Lane 3 using N-dodecyl-β-D-maltoside (DM), Lane 4 using digitonin, Lane 5 using Triton-X100, Lane 6 using Nonidet-P40, Lane 7 using polyoxyethylene 8 lauryl ether ($C_{12}E_8$), Lane 8 using polyoxyethylene 23 lauryl ether (Bruj35), Lane 9 using Tween 20, Lane 10 using Tween 40, Lane 11 using Tween 60, Lane 12 using Tween 80, Lane 13 using HECAMEG, Lane 14 using CHAPS, Lane 15 using deoxycholic acid, Lane 16 using sodium cholate, Lane 17 using sodium dodecyl sulfate (SDS) and Lane 18 using N-laurylsarcosine. Each detergent was added at a concentration of 1% or less. FIG. 11B shows the results of the optimization for the concentration of digitonin and Brij35, with a solid bar representing a total synthesized protein level and an open bar representing a supernatant protein level.

Based on the results shown in FIG. 11A, Brij35 and digit on in suppressed the aggregation of the synthesized membrane proteins effectively. The proteins synthesized in the reaction solutions containing Brij35 at 0.05% or higher and digitonin at 0.2% or higher mostly remained in the supernatant fractions of the centrifugation (see FIG. 11B). Although these detergents increased the soluble protein levels, they had no effects on the expression levels. On the contrary, CHAPS, cholic acids and OG suppressed the protein synthesis completely, and Triton-X100 had almost no effect on the solubilization (solubility). While Brij35 (Lane 8) and $C_{12}E_8$ (Lane 7) are the nonionic detergents having analogous chemical structures, they exhibited the effects on the solubility of the synthesized proteins which were quite different by the length of the lauryl ether chain length.

Figure 12A:
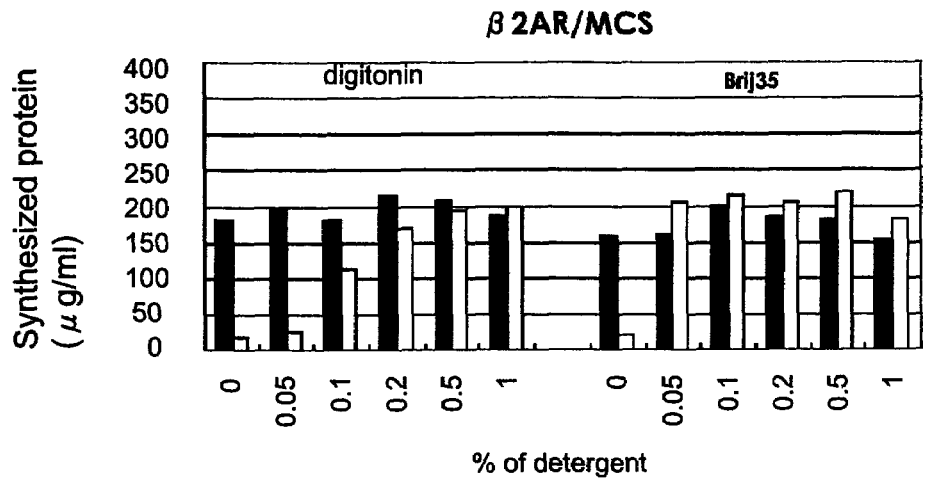
FIG. 12 A-C shows the results of the synthesis of β2AR cloned into any of three expression vectors in a cell-free protein synthesis system by a batch method using various detergent levels.
Figure 12B:
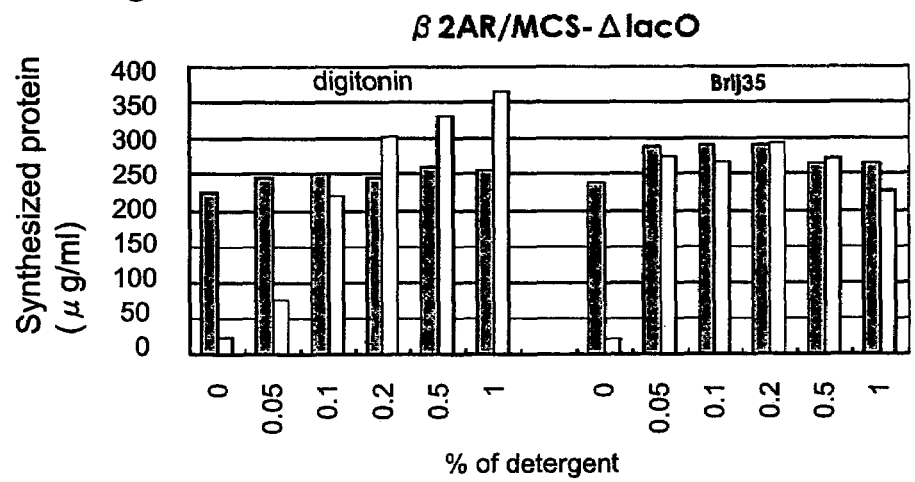
Figure 12C:
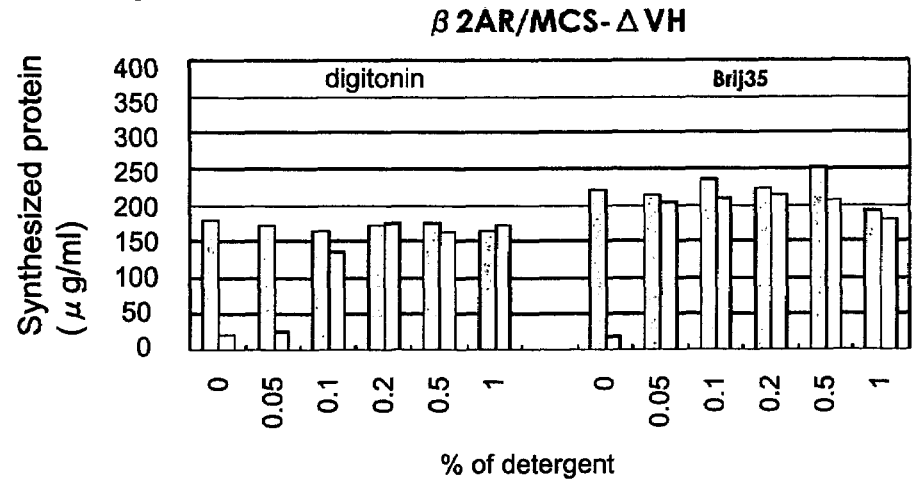

Also the effects of the addition of digitonin and Brij35 were verified using three expression vectors β2AR/MCS, β2AR/MCS-ΔlacO and β2AR/MCS-ΔVH. The results are show in FIG. 12A-C. The use of the template DNA having the deletion of the lactose operator sequence (β2AR/MCS-ΔlacO) resulted in not only an increase in the total amount of the protein synthesized in the cell-free protein synthesis system but also a marked improvement in the solubility of the synthesized proteins due to the addition of digitonin or Brij35 (see FIG. 12B).

(4) Investigation of Amount of β2AR-Gs Synthesized by Dialysis Method

Using 4.5 ml of an internal reaction solution having the composition indicated in Table 2 shown below and 45 ml of an external reaction solution having the composition indicated in Table 3, protein synthesis was conducted by a dialysis method. A 0.9 ml aliquot of the internal reaction solution was dispensed into each of 5 dialysis membranes (Spectra/Por, fractionating molecular weight 50,000), which was allowed to float in the external reaction solution whereby effecting the protein synthesis for a period of 8 hours at maximum at 30° C.

TABLE 2

Composition of internal reaction solution

| Composition | Concentration |
| --- | --- |
| HEPES-KOH pH 7.5 | 58.0 mM |
| Dithiothreitol (DTT) | 1.8 mM |
| ATP | 1.2 mM |
| CTP, GTP, UTP | each 0.9 mM |
| Creatine phosphate | 81.0 mM |
| Creatine kinase | 0.25 mg/ml |
| Polyethylene glycol 8000 | 4.0% |
| 3',5'-cAMP | 0.64 mM |
| L-(−)-5-formyl-5,6,7,8-tetrahydrofolic acid | 35.0 μg/ml |
| E. coli total tRNA | 170.0 μg/ml |
| Potassium glutamate | 200.0 mM |
| Ammonium acetate | 27.7 mM |
| Magnesium acetate | 10.7 mM |
| Amino acid (20 types) | each 1.5 mM |
| Sodium azide | 0.05% |
| T7RNA Polymerase | 16.0 units/μl |
| E. coli S30 extract solution (BL21 Codon Plus) | 1.08 ml/4.5 ml |
| Template DNA | 10 μg/ml |
| Digitonin | 0.2% |
| Liposome (lipid vesicle)*[1] | 12.5 μl/ml |

*[1]Produced by mixing each 25 mg of egg yolk phosphatidylcholin (PC), bovine brain phosphatidylserine (PS), bovine brain phosphatidylethanolamine (PE) and dipalmitoyl phosphatidylcholine (DPPC) (all Sigma) and using Avanti mini-extruder (Avanti Polar Lipids).The particle size was made uniform by passing through an extruder membrane whose diameter was 100 nm. The uniform mixture was re-suspended in 800 μl of distilled water and used as a liposome (lipid vesicle).

TABLE 3

Composition of external reaction solution

| Composition | Concentration |
| --- | --- |
| HEPES-KOH pH 7.5 | 58.0 mM |
| Dithiothreitol (DTT) | 2.3 mM |
| ATP | 1.2 mM |
| CTP, GTP, UTP | each 0.9 mM |
| Creatine phosphate | 81.0 mM |
| Polyethylene glycol 8000 | 4.0% |
| 3',5'-cAMP | 0.64 mM |
| L-(−)-5-formyl-5,6,7,8-tetrahydrofolic acid | 35.0 μg/ml |
| Potassium glutamate | 200.0 mM |
| Ammonium acetate | 27.7 mM |
| Magnesium acetate | 10.7 mM |
| Amino acid (20 types) | each 1.5 mM |
| Sodium azide | 0.05% |
| Tris acetate (pH 8.2) | 4.2 mM |
| Potassium acetate | 3.0 mM |
| Digitonin | 0.4% |

Figure 13A:
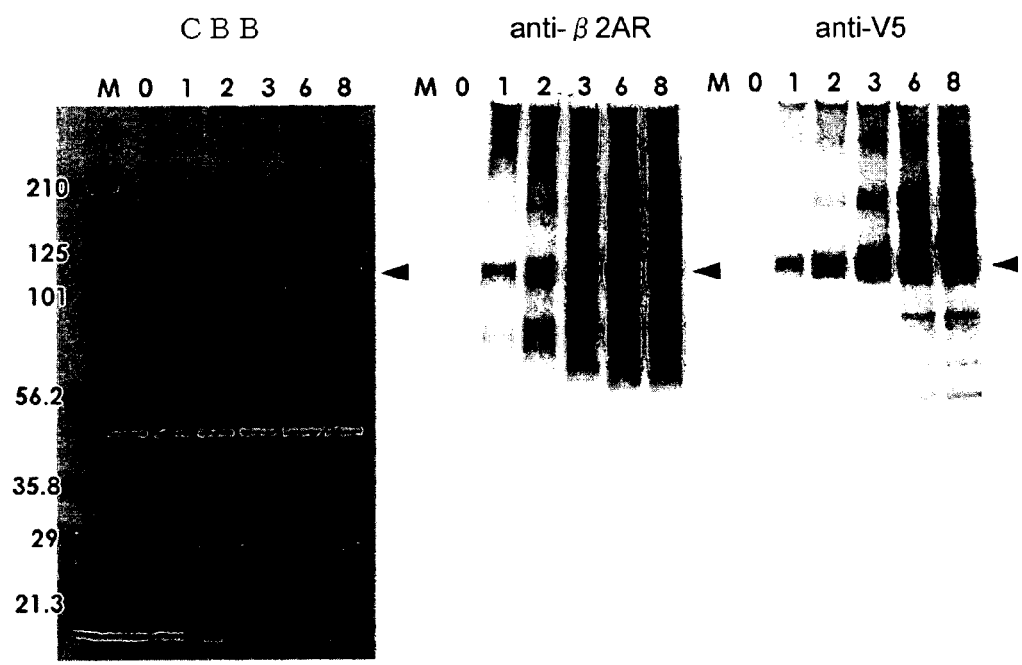
FIG. 13A shows the results of western blotting of 1 µl of synthesis reaction mixture separated by a 4 to 20% gradient gel followed by detection with Coomassie brilliant blue (CBB) staining, anti-β2AR antibody (anti-β2AR) or anti-V5 antibody (anti-V5).
Figure 13B:
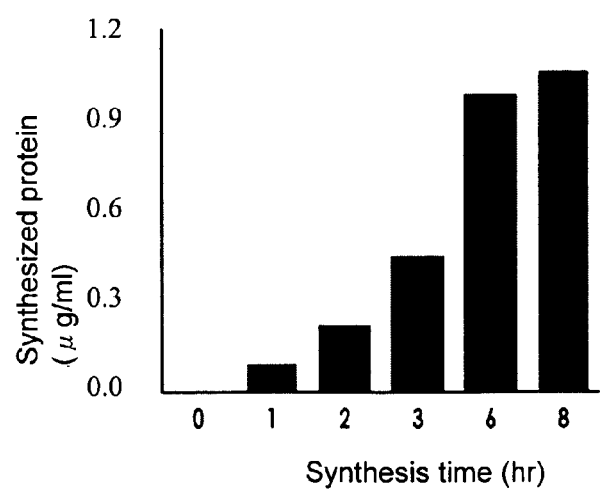
FIG. 13B shows the expression levels at 0, 1, 2, 3, 6 and 8 hours after initiation of the synthesis reaction.

After initiation of the dialysis, a 25 μl sample for the electrophoresis was taken at intervals for a period of 8 hours at maximum. After removing impurities by acetone precipitation, followed by centrifugation of 15,000 rpm at 4° C. for 10 minutes, the precipitate was recovered. The precipitate was dried, combined with 8M urea and SDS-PAGE sample buffer and dissolved. Each sample (corresponding to 1 μl of the synthesis reaction solution) was subjected to SDS-PAGE by a standard method using 4 to 20% gradient gel, stained with Coomassie brilliant blue (CBB) or SYPRO Orange (Molecular Probes), or subjected to a western blotting analysis using anti-β2AR antibody or anti-V5 antibody. The results are shown in FIG. 13A. In FIG. 13A, M represents a molecular weight marker, and 1 to 8 represent respective synthesis time. The β2AR-Gs fused with the thioredoxin began to be observed 1 hour after initiation of the synthesis at an estimated molecular weight of about 109 kDa by a CBB staining, and the amount synthesized continued to be increased over a period of 8 hours. The synthesized thioredoxin-fused protein was verified by the immune reactivity with the anti-β2AR antibody and/or anti-V5 antibody. On the other hand, SDS-PAGE was conducted together with bovine serum albumin (BSA) at a known concentration and then the gel was stained with SYPRO Orange, and the image was captured using a BioRad Molecular Imager FX, and a standard curve was obtained based on the correlation between the BSA protein concentration (0.025 to 0.4 mg/ml) and the band intensity. The amount of the thioredoxin-fused β2AR-Gs synthesized was calculated as a BSA amount based on the band intensity. As an analytical software, Quantity one was employed. The results are shown in FIG. 13B. As shown in FIG. 13B, the synthesis reaction in the cell-free protein synthesis system by the dialysis method exhibited a continuous increase in the synthesis rate over 8 hours, indicating that the thioredoxin-fused GPCR, which is a large membrane protein having a molecular weight of 100 kDa or higher, can be synthesized at a scale as large as 1 mg/ml for 6 to 8 hours.

(5) Reconstitution of β2AR-Gs and Ligand Binding Ability Measurement

After conducting the protein synthesis reaction by the dialysis method described above for 6 hours, the internal reaction solution was supplemented with N-lauroylsarcosine at 0.5%, and ultrasonicated for 1 minutes. Subsequently, PBS was added to dilute the detergent, and 10% β-dodecylmaltoside (Nacalaitesque) was added dropwise to make the final concentration 1%. A 1 ml aliquot of this solution was combined with 12.5 μl of the liposome which was the same to that employed in the cell-free protein synthesis system described above, transferred into a dialysis membrane (Spectra/Por, fractionating molecular weight 50,000), which was dialyzed in a phosphate buffer solution supplemented with 1% CARBIOSORB (Carbiochem) while exchanging the buffer solution at an interval of 6 to 12 hours at 4° C. for three to four days. A complex of the reconstituted thioredoxin-fused β2AR-Gs after completion of the dialysis and the liposome was centrifuged for 1 hours at 100,000×g and 4° C., and the resultant precipitation fraction (reconstituted membrane fraction) was suspended in 50 μl of an incubation buffer (75 mM Tris-HCl (pH7.4), 12.5 mM $MgCl_2$, 2 mM EDTA).

The ligand binding saturation experiment was conducted by incubating this reconstituted membrane fraction (complex of thioredoxin-fused β2AR-Gs and liposome) together with 0 to 25 nM tritium-labeled Dihidroalprenolol ([$^3$H] DHA) in 200 μl as a final volume of the incubation buffer at 25° C. for 60 minutes. A competition experiment was conducted by incubating the reconstituted membrane fraction described above together with 10 nM [$^3$H]DHA in the presence or absence of $10^{-8}$ to $10^{-2}$ MAlprenolol (Sigma).

A 96-well Unifilter GF/C (Whatman) was provided and washed preliminarily twice with 200 μl of 0.3% polyethyleneimine and then 9 times with 200 μl 50 mM Tris-HCl (pH7.4). This 96-well Unifilter was filled with the reaction solution described above, and then washed 5 times with the incubation buffer. Thereafter, the 96-well Unifilter was dried and each well was filled with 50 μl of MicroScint-O (Packard) and allowed to stand for 10 minutes in a dark place. Each well was examined for the radioactivity attributable to the [$^3$H]Dihidroalprenolol using a TOPCOUNT (Pakcard). Based on the results obtained, a saturation curve (FIG. 14A) and a competition curve (FIG. 14B) were obtained and the binding constant (Kd value) was calculated using a GraphPad PRIZM 3.03 (Graph pad Software).

Figure 14A:
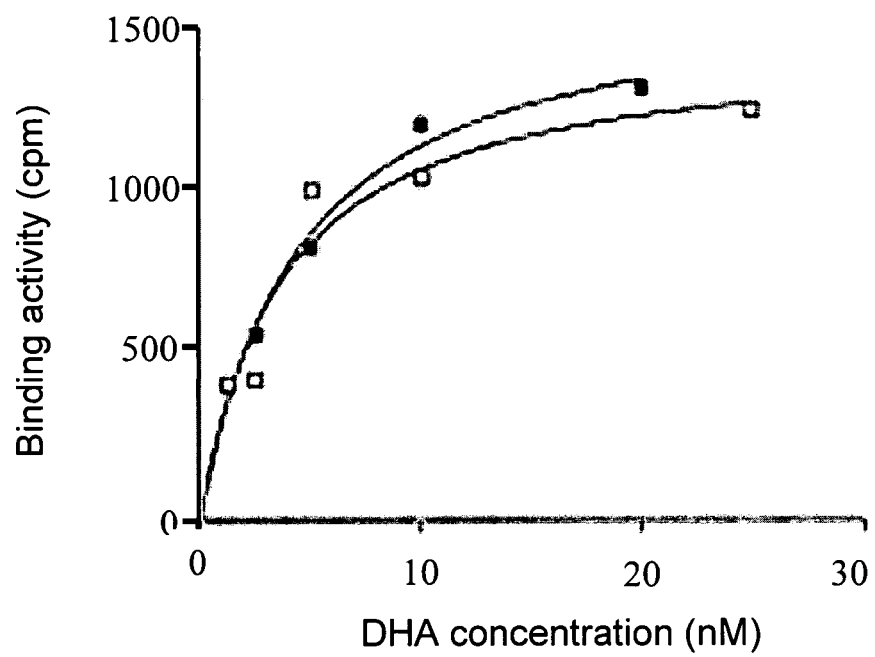
FIG. 14A shows the ligand binding saturation curve of β2AR-Gs which was synthesized in a cell-free protein synthesis system and formed a complex with liposome (■) and β2AR which was expressed in Sf9 cell (□).
Figure 14B:
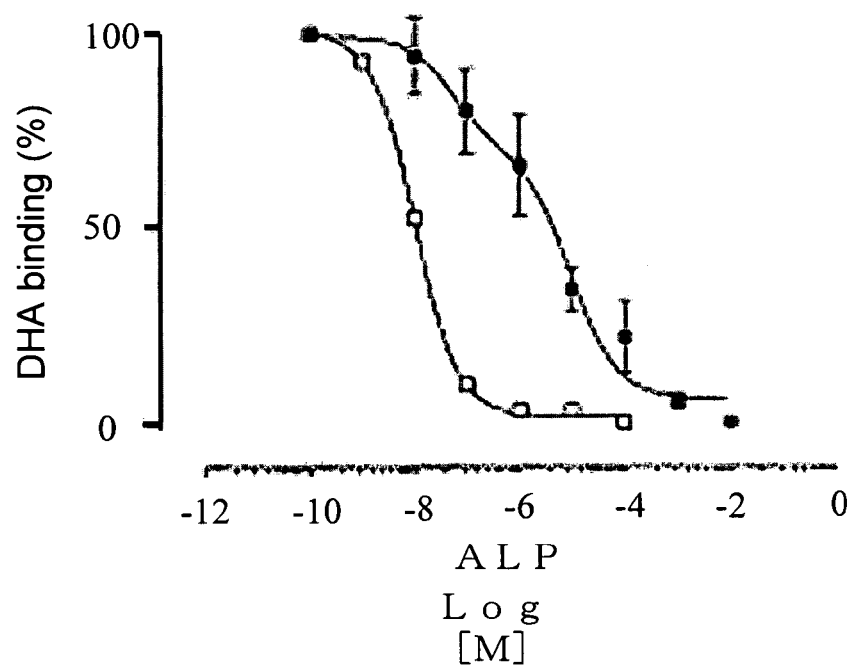
FIG. 14B shows the competition curve for aiprenolol of β2AR-Gs which was synthesized in a cell-free protein synthesis system and formed a complex with liposome (■) and β2AR which was expressed in Sf9 cell (□). Each data point is a mean of the duplicate measurements.

As evident from FIG. 14A, the synthesized thioredoxin-fused β2AR-liposome complex has an ability of binding to the [$^3$H]DHA which is the ligand, and this fused protein has a correct three dimensional structure similar to that when it exists on the cell membrane, thus being beneficial practically in biochemical or structural scientific researches. Based on the results of three independent experiments, the highest Kd value was 4.3 nM, and the average was 5.5±1.1 nM. The Kd value of the human β2AR expressed in an insect cell (Sf9 cell) employed as a positive control was 3.9 nM (n=1). FIG. 14B is the competitive ligand concentration examined using $10^{-8}$ to $10^{-2}$ M alprenolol. The EC50 values of the thioredoxin-fused β2AR-liposome complex (concentration of ligand causing 50% inhibition) for the competitions at 2 binding sites and 1 binding site were $2.2×10^{-8}$ M and $1.0×10^{-5}$ M (n=5), respectively, indicating a slightly lower alprenolol sensitivity when compared with the EC50 value of the human β2AR expressed in the Sf9 cell ($1.0×10^{-8}$ M, n=1). Based on these results, it was revealed that the β2AR expressed as being fused with the thioredoxin in the cell-free protein synthesis system has a DHA binding activity when being reconstituted as a complex with the liposome, although the activity is slightly lower than that of the human β2AR expressed in the Sf9 cell. The presence of the region derived from the thioredoxin is assumed to have no substantial effect on a fused protein ligand binding activity.

INDUSTRIAL APPLICABILITY

By the method of the present invention, a highly hydrophobic protein such as a membrane protein can be synthesized in a cell-free protein synthesis system very efficiently and at a large scale as a fused protein with a thioredoxin. A synthesized fusion protein can readily be solubilized, and can exhibit its original biological activity. Since these results suggest that a protein synthesized by the method of the present invention forms a correct three dimensional structure, it is possible to be used for an application to a three dimensional structural analysis or intracellular functional analysis. Through such an analysis, the method of the present invention is very useful in developing pharmaceuticals.

The invention claimed is:

1. A method for expressing a thioredoxin-fused membrane protein comprising: expressing said thioredoxin-fused protein in a cell-free protein synthesis system, wherein said cell-free protein synthesis system comprises a non-ionic detergent and wherein said non-ionic detergent is present at a concentration of from 1 to 50 times the critical micellar concentration of said non-ionic detergent during expression of the thioredoxin-fused membrane protein.

2. The method of claim 1, wherein said non-ionic detergent is selected from the group consisting of digitonin, polyoxyethylene 23 lauryl ether and a combination thereof.

3. The method of claim 1, wherein said thioredoxin-fused membrane protein can be synthesized at a synthetic yield of at least 100 µg/ml within a reaction period of 8 hours in said cell-free protein synthesis system.

4. The method of claim 1, wherein said membrane protein is a guanine nucleotide binding protein-coupled receptor.

5. A method for expressing a membrane protein comprising: expressing a fusion protein wherein thioredoxin is fused with said membrane protein and wherein the fusion protein comprises a specific sequence capable of being cleaved by a protease between the thioredoxin and the fused membrane protein, in a cell-free protein synthesis system, and isolating said membrane protein by limited cleavage of thioredoxin moiety of said fusion protein; wherein said cell-free protein synthesis system comprises a non-ionic detergent and wherein said non-ionic detergent is present at a concentration of from 1 to 50 times the critical micellar concentration of said nonionic detergent during expression of the fusion protein.

6. The method of claim 5, wherein said non-ionic detergent selected from the group consisting of digitonin, polyoxyethylene 23 lauryl ether and a combination thereof.

7. The method of claim 5, wherein said thioredoxin-fused membrane protein can be synthesized at a synthetic yield of at least 100 µg/ml within a reaction period of 8 hours in said cell-free protein synthesis system.

8. The method of claim 5, wherein said membrane protein is a guanine nucleotide binding protein-coupled receptor.

9. A method for producing a complex of a thioredoxin-fused membrane protein and a liposome comprising: expressing a ligated gene comprising a nucleotide sequence encoding the thioredoxin and a nucleotide sequence encoding the membrane protein in a cell-free protein synthesis system; mixing the thioredoxin-fused membrane protein expressed in said cell-free protein synthesis system with a non-ionic detergent and a liposome whose particle size is uniform; and reducing the concentration of said non-ionic detergent in said mixture.

10. The method of claim 9, wherein the particle size of said liposome is within the range of 50 to 200 nm.

11. The method of claim 9, wherein said membrane protein is a guanine nucleotide binding protein-coupled receptor.

12. The method of claim 11, wherein the thioredoxin-fused guanine nucleotide binding protein-coupled receptor in said complex has a function of mediating signal transduction of said receptor.

13. The method of claim 12, wherein a ligand is able to bind to said receptor.

14. The method of claim 9, wherein said non-ionic detergent is selected from the group consisting of: digitonin, polyoxyethylene 23 lauryl ether and a combination thereof.

15. A method for expressing a thioredoxin-fused membrane protein comprising: expressing said thioredoxin-fused membrane protein in a cell-free protein synthesis system that comprises digitonin or polyoxyethylene 23 lauryl ether, wherein non-ionic detergent digitonin or polvoxvethylene 23 lauryl ether, is present at a concentration of from 1 to 50 times the critical micellar concentration of said nonionic detergent during expression of the thioredoxin-fused membrane protein.

16. A polynucleotide for expressing a fusion protein in a cell-free protein synthesis system, said polynucleotide comprising a thioredoxin gene linked via a ribosome binding site downstream of a T7 promoter sequence and a membrane protein gene linked with said thioredoxin gene to be expressed as a fusion protein, wherein no operator sequence is operatively linked to said promoter sequence, and wherein said membrane protein gene is a guanine nucleotide binding protein coupled receptor gene.

* * * * *

SEQUENCE LISTING

```
<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Synthetic 5' PCR primer MT43NTR

<400> SEQUENCE: 1
caccatgacc tcggaatccg acacggcagg gcccaac                              37

<210> SEQ ID NO 2
<211> LENGTH: 20
<212> TYPE: DNA
<213> ORGANISM: Artificial Sequence
<220> FEATURE:
<223> OTHER INFORMATION: Synthetic 3' PCR primer

<400> SEQUENCE: 2
gtacagggtc tcccgggtgg                                                 20
```

<210> SEQ ID NO 3
<211> LENGTH: 32
<212> TYPE: DNA
<213> ORGANISM: Artificial Sequence
<220> FEATURE:
<223> OTHER INFORMATION: Synthetic 5' PCR primer MBP-T43NTR

<400> SEQUENCE: 3
caccatgaaa ataaaaacag gtgcacgcat cc                          32

<210> SEQ ID NO 4
<211> LENGTH: 26
<212> TYPE: DNA
<213> ORGANISM: Artificial Sequence
<220> FEATURE:
<223> OTHER INFORMATION: Synthetic 5' oligonucleotide primer

<400> SEQUENCE: 4
caccatggat gactccacgg actcct                                 26

<210> SEQ ID NO 5
<211> LENGTH: 30
<212> TYPE: DNA
<213> ORGANISM: Artificial Sequence
<220> FEATURE:
<223> OTHER INFORMATION: Synthetic 3' oligonucleotide primer for m2

<400> SEQUENCE: 5
ccttgtagcg cctatgttct tataatgaca                             30

<210> SEQ ID NO 6
<211> LENGTH: 26
<212> TYPE: DNA
<213> ORGANISM: Artificial Sequence
<220> FEATURE:
<223> OTHER INFORMATION: Synthetic oligonucleotide PCR forward primer

<400> SEQUENCE: 6
caccatgggg caacccggga acggca                                 26

<210> SEQ ID NO 7
<211> LENGTH: 23
<212> TYPE: DNA
<213> ORGANISM: Artificial Sequence
<220> FEATURE:
<223> OTHER INFORMATION: Synthetic oligonucleotide PCR reverse primer
      for b2ARGs

<400> SEQUENCE: 7
tggaggcagt catactcgac gag                                    23

<210> SEQ ID NO 8
<211> LENGTH: 29
<212> TYPE: DNA
<213> ORGANISM: Artificial Sequence
<220> FEATURE:
<223> OTHER INFORMATION: Synthetic oligonucleotide PCR reverse primer
      for b2AR

<400> SEQUENCE: 8
ccttaacatc atgtttactg agtgacgac                              29

<210> SEQ ID NO 9
<211> LENGTH: 54
<212> TYPE: DNA

-continued

```
<213> ORGANISM: Artificial Sequence
<220> FEATURE:
<223> OTHER INFORMATION: Synthetic oligonucleotide for MCS

<400> SEQUENCE: 9
gttaacgaat tcgtcgacgg taccccatgg actagtcacg tgcggccgct cgag        54

<210> SEQ ID NO 10
<211> LENGTH: 17
<212> TYPE: DNA
<213> ORGANISM: Artificial Sequence
<220> FEATURE:
<223> OTHER INFORMATION: Synthetic 17 bp sequence of the mutated lactose
      operator vector

<400> SEQUENCE: 10
gagaccacaa cggtttc                                                  17

<210> SEQ ID NO 11
<211> LENGTH: 28
<212> TYPE: DNA
<213> ORGANISM: Artificial Sequence
<220> FEATURE:
<223> OTHER INFORMATION: Synthetic PCR 5' primer

<400> SEQUENCE: 11
gagaattcat ggggcaaccc gggaacgg                                      28

<210> SEQ ID NO 12
<211> LENGTH: 28
<212> TYPE: DNA
<213> ORGANISM: Artificial Sequence
<220> FEATURE:
<223> OTHER INFORMATION: Synthetic PCR 3' primer

<400> SEQUENCE: 12
ctctcgagca gcagtgagtc atttgtac                                      28
```